US011331326B2

(12) United States Patent
Song et al.

(10) Patent No.: US 11,331,326 B2
(45) Date of Patent: May 17, 2022

(54) COMPOSITION FOR PREVENTION OR TREATMENT OF INFLAMMATORY SKIN DISEASES OR SEVERE PRURITUS COMPRISING THE AQUEOUS SOLUBILIZED URSODEOXYCHOLIC ACID

(71) Applicant: AMICOGEN PHARMA INC., Seongnam-si (KR)

(72) Inventors: Yeong Ho Song, Seoul (KR); Hwi Jin Ko, Seoul (KR)

(73) Assignee: Amicogen Pharma Inc., Seongnam-si (KR)

( * ) Notice: Subject to any disclaimer, the term of this patent is extended or adjusted under 35 U.S.C. 154(b) by 0 days.

(21) Appl. No.: 16/221,303

(22) Filed: Dec. 14, 2018

(65) Prior Publication Data
US 2019/0192539 A1    Jun. 27, 2019

Related U.S. Application Data

(63) Continuation of application No. PCT/KR2017/010893, filed on Sep. 28, 2017.

(30) Foreign Application Priority Data

Sep. 30, 2016   (KR) ........................ 10-2016-0126872
Sep. 27, 2017   (KR) ........................ 10-2017-0125571

(51) Int. Cl.
| A61K 31/575 | (2006.01) |
| A61K 47/36  | (2006.01) |
| A61K 9/00   | (2006.01) |
| A61Q 19/00  | (2006.01) |
| A61K 8/63   | (2006.01) |
| A61K 8/73   | (2006.01) |
| A61K 9/06   | (2006.01) |
| A61P 17/10  | (2006.01) |
| A61P 17/06  | (2006.01) |
| A61P 17/04  | (2006.01) |
| A61K 9/70   | (2006.01) |

(52) U.S. Cl.
CPC ............. *A61K 31/575* (2013.01); *A61K 8/63* (2013.01); *A61K 8/732* (2013.01); *A61K 9/0014* (2013.01); *A61K 9/06* (2013.01); *A61K 9/7007* (2013.01); *A61K 47/36* (2013.01); *A61P 17/04* (2018.01); *A61P 17/06* (2018.01); *A61P 17/10* (2018.01); *A61Q 19/00* (2013.01)

(58) Field of Classification Search
CPC ........ A61K 31/575; A61K 8/63; A61K 8/732; A61K 9/0014; A61K 9/06; A61K 47/36; A61P 17/04; A61P 17/06; A61P 17/10; A61Q 19/00
See application file for complete search history.

(56) References Cited

U.S. PATENT DOCUMENTS

| 4,185,099 | A   |   | 1/1980  | Sorbini |
| 4,866,049 | A   |   | 9/1989  | Maumenee et al. |
| 6,251,428 | B1  | * | 6/2001  | Yoo ...................... A61K 9/0014 424/455 |
| 6,562,363 | B1  | * | 5/2003  | Mantelle .............. A61K 9/0014 424/434 |
| 7,052,716 | B1  |   | 5/2006  | Lanzendorfer et al. |
| 2003/0186933 | A1 |   | 10/2003 | Yoo |
| 2005/0158408 | A1 | * | 7/2005  | Yoo ...................... A61K 9/0014 424/728 |
| 2006/0051319 | A1 |   | 3/2006  | Yoo |
| 2006/0142241 | A1 | * | 6/2006  | Yoo ...................... A61K 9/0095 514/59 |
| 2007/0072828 | A1 |   | 3/2007  | Yoo |
| 2008/0194531 | A1 |   | 8/2008  | Steer et al. |
| 2009/0074895 | A1 |   | 3/2009  | Mikov et al. |
| 2013/0281420 | A1 |   | 10/2013 | Taraporewala et al. |
| 2014/0323455 | A1 |   | 10/2014 | Vavvas |
| 2016/0175324 | A1 |   | 6/2016  | Dayan et al. |
| 2016/0303240 | A1 |   | 10/2016 | Oki et al. |

FOREIGN PATENT DOCUMENTS

| CN | 1348360 A   | 5/2002  |
| CN | 103070948 A | 5/2013  |
| CN | 102178784 B | 6/2013  |
| CN | 104083381 A | 10/2014 |

(Continued)

OTHER PUBLICATIONS

Lee, Seung Yong et al., "Comparison of Physicochemical Properties between Ursodeoxycholic Acid and Chemodeoxycholic Acid Inclusion Complexes with P-Cydodextrin," Yakhak Hoeji, 1994, vol. 38, No. 3, pp. 300-310.

Woo, Se Joon et al., "Ursodeoxycholic Acid and Tauroursodeoxycholic Acid Suppress Choroidal Neovascularization in a Laser-Treated Rat Model," Journal of Ocular Pharmacology and Therapeutics, vol. 26, No. 3, 2010.

Office Action received in Korean Patent Application No. 10-2018-0015944, dated Feb. 19, 2019.

International Search Report received in PCT Application No. PCT/KR2018/001770, dated Jun. 7, 2018.

International Search Report received in PCT Application No. PCT/KR2017/010893, dated Jan. 15, 2018.

Office Action received in Korean Patent Application No. 10-2017-0125571, dated Nov. 9, 2018.

(Continued)

*Primary Examiner* — Shobha Kantamneni

(74) *Attorney, Agent, or Firm* — Knobbe Martens Olson & Bear LLP

(57) ABSTRACT

This disclosure relates to a composition for the prevention or the treatment of inflammatory skin diseases or severe pruritus comprising an aqueous solubilized ursodeoxycholic acid (UDCA). According to this disclosure, inflammatory skin diseases and severe pruritus such as atopic dermatosis, acne, psoriasis, hives, inflammatory skin disease, seborrheic dermatitis and contact dermatitis can be effectively alleviated or treated. Therefore, the composition comprising aqueous solubilized ursodeoxycholic acid of this disclosure can be best used as a pharmaceutical, food or cosmetic composition, and can be used particularly as an external preparation to exhibit its effect.

5 Claims, 19 Drawing Sheets

(56) References Cited

FOREIGN PATENT DOCUMENTS

| | | | |
|---|---|---|---|
| EP | 0720854 A1 | | 7/1996 |
| JP | H10-017474 A | | 1/1998 |
| JP | H10-120579 A | | 5/1998 |
| JP | 2002-522357 | | 7/2002 |
| JP | 2002-533366 A | | 10/2002 |
| JP | 2003-526602 A | | 9/2003 |
| JP | 2008-521800 | | 6/2008 |
| JP | 2015-143217 A | | 8/2015 |
| KR | 2001-0074748 | | 8/2001 |
| KR | 10-2003-0003952 | | 1/2003 |
| KR | 2003-0003952 | | 1/2003 |
| KR | 10-2007-0053238 A | | 5/2007 |
| KR | 2007-0098821 | | 10/2007 |
| KR | 10-2008-0012258 A | | 2/2008 |
| KR | 101272792 | * | 6/2013 |
| KR | 10-1645355 | | 8/2016 |
| KR | 10-2016-0108554 A | | 9/2016 |
| RU | 2277913 C2 | | 6/2006 |
| WO | WO 2000/004875 A2 | | 2/2000 |
| WO | WO 2006/026555 A2 | | 3/2006 |
| WO | WO 2006/086452 A1 | | 8/2006 |
| WO | WO 2010/123156 A1 | | 10/2010 |
| WO | WO 2013/025840 A1 | | 2/2013 |

OTHER PUBLICATIONS

Australian Office Action dated Aug. 16, 2019, related to Australian Patent Application No. 2018218696.
Canadian Office Action dated Feb. 19, 2020, related to Canadian Patent Application No. 3032072.
Chinese Office Action dated Apr. 20, 2020, related to Chinese Patent Application No. 201780045135.1.
Indian Office Action dated Jan. 30, 2020, related to Indian Patent Application No. 201917014353.
Indian Office Action dated Feb. 24, 2020, related to Indian Patent Application No. 201917012229.
Itoh et al. Psoriasis treated with ursodeoxycholic acid: three case reports. Clinical and Experimental Dermatology, 32, 398-400.
Joutsiniemi et al. Intrahepatic cholestasis of pregnancy: observational study of the treatment with low-dose ursodeoxycholic acid. BMC Gastroenterology (2015) 15:92.
Russian Office Action dated Dec. 4, 2019, related to Russian Patent Application No. 2019111077.
U.S. Office Action dated May 6, 2020, issued in related U.S. Appl. No. 16/400,969.
Office Action dated Apr. 7, 2020 in Japanese Application No. 2019-520858, in 8 pages.
Office Action dated Apr. 28, 2020 in Canadian Application No. 3,039,500, in 4 pages.
International Preliminary Report on Patentability dated Aug. 13, 2019 in International Application No. PCT/KR2018/001770, in 7 pages.
Chung et al., "Ursodeoxycholic Acid Attenuates Endoplasmic Reticulum Stress-Related Retinal Pericyte Loss in Streptozotocin-Induced Diabetic Mice," *Journal of Diabetes Research*, vol. 2017, Article ID 1763292, 2017, 10 pages.
Office Action received in JP2019-520351 dated Nov. 5, 2019.
"Spot News", Fragrance Journal: The Magazine of Research & Development for Cosmetics, Toiletries & Allied Industries, vol. 33, No. 11—7 pages (2005).
Office Action of Japanese Patent Application No. 2019-520351—11 pages (dated Sep. 8, 2020).
Chinese Office Action of Chinese Patent Application No. 201780045135. 1—5 pages (dated Feb. 2, 2021).
Korean Office Action of Korean Patent Application No. 10-2019-0104669—5 pages (dated Feb. 4, 2021).
Extended European Search Report of Patent Application No. 18751361. 9—9 pages (dated Sep. 28, 2020).
Japanese Office Action of Japanese Patent Application No. 2019-520858—5 pages (dated Nov. 24, 2020).
Kovach et al., "Anti-VEGF Treatment Strategies for Wet AMD", Journal of Ophthalmology—7 pages (2012).
Mexican Office Action of Mexican Patent Application No. MX/a/2019/008963—6 pages (dated Oct. 19, 2020).
U.S. Final Office Action dated Dec. 8, 2020, in U.S. Appl. No. 16/400,969.

* cited by examiner

1: pH 9.5(Clear), 2: pH 8.9(Clear), 3: pH 7.9(Clear), 4: pH 7.1(Clear),
5: pH 6.0(Clear), 6: pH 5.5(Precipitates, not Clear)

From left test tube pH 9.4(Clear), pH 7.1(Clear), 6.1(Clear), pH 5.5(Clear), pH 5.1(Precipitates, not Clear)

From left test tube pH 9.6(Clear), pH 6.1(Clear), pH5.1(Clear), pH 4.0(Precipitates, not Clear)

1: pH 9.0(Clear), 2: pH 8.0(Clear), 3: pH 7.0(Clear), 4: pH 6.0(Clear), 5: pH 5.1(Clear), 6: pH 4.1(Clear), 7: pH 2.9(Clear)

1: pH 10.2(Clear), 2: pH 9.0(Clear), 3: pH 8.1(Clear), 4: pH 7.1(Clear),
5: pH 6.1(Clear), 6: pH 5.1(Clear), 7: pH 4.1(Clear), 8: pH 2.9(Clear)

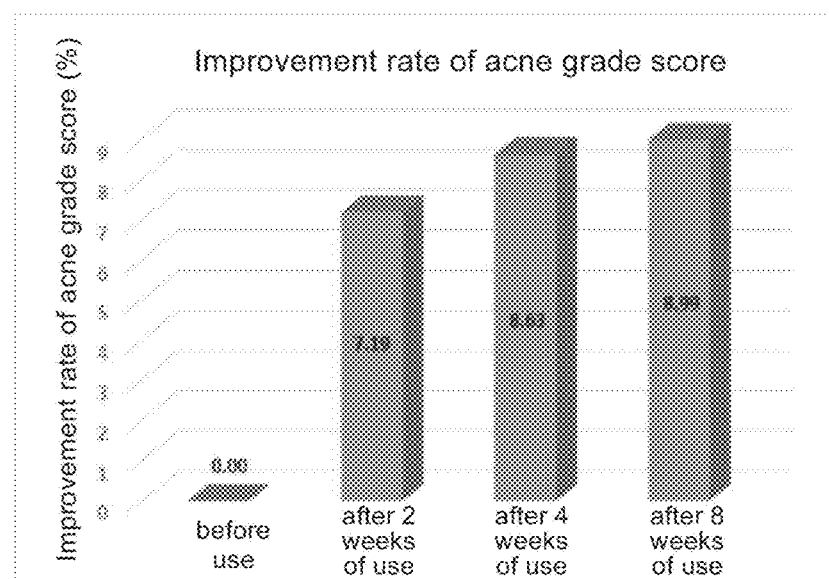

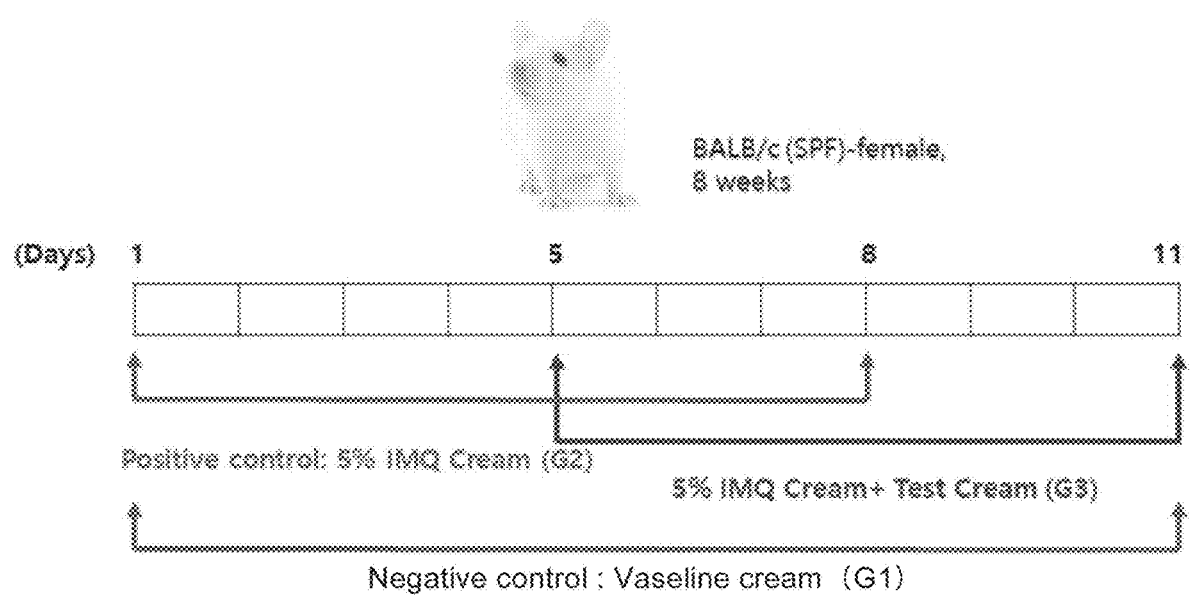

COMPOSITION FOR PREVENTION OR TREATMENT OF INFLAMMATORY SKIN DISEASES OR SEVERE PRURITUS COMPRISING THE AQUEOUS SOLUBILIZED URSODEOXYCHOLIC ACID

CROSS-REFERENCE TO RELATED APPLICATIONS

This application is a continuation application, and claims the benefit under 35 U.S.C. § 120 and § 365 of PCT Application No. PCT/KR2017//010893, filed on Sep. 28, 2017, which is hereby incorporated by reference. PCT/KR2017/010893 also claimed priority from Korean Patent Application No. 10-2016-0126872 filed on Sep. 30, 2016 and Korean Patent Application No. 10-2017-0125571 filed on Sep. 27, 2017, both of which are hereby incorporated by reference.

FIELD

This disclosure relates to a composition for prevention or treatment of inflammatory skin diseases or severe pruritus comprising aqueous solubilized ursodeoxycholic acid (UDCA). More particularly, this disclosure relates to a pharmaceutical composition excellent for prevention or treatment of inflammatory skin diseases or severe pruritus such as atopic skin diseases, acne, psoriasis, hives, inflammatory dermatitis, seborrheic dermatitis and contact dermatitis, and a skin external preparation for alleviating symptoms of inflammatory skin diseases.

DESCRIPTION OF RELATED TECHNOLOGY

Atopic dermatitis, acne, psoriasis, hives, allergic contact dermatitis or irritant contact dermatitis and seborrheic dermatitis are very typical inflammatory skin diseases, involving local inflammatory edema and hyperkeratosis, and intolerable pruritus.

Recently, the incidence of hypersensitive or inflammatory skin diseases has been greatly increased due to changes in the living environment such as industrialization and western-style eating habits. In the case of those suffering from inflammatory skin diseases, patients should endure a long period of treatment and resulting high cost associated with it. Patients may be passive to external activities due to the disease and in worst case may have severe obesity and depression. The most widely known inflammatory skin diseases are atopic skin diseases, acne and psoriasis.

Atopic dermatitis is a long-lasting chronic dermatitis, usually occurring at 2 to 3 months of age. Characteristics of atopic dermatitis are the appearance of severe itchy eczema lesions on the skin, and if symptoms occur, patients are scratching or rubbing the area, resulting in worsening skin symptoms. The number of patients of atopic dermatitis is increasing worldwide. By the 1970s, about 3% of children under 6 years of age were reported to have atopic dermatitis. However, it is estimated that recently, about 20% of children and about 1 to 3% of adults have atopic dermatitis. In addition, atopic dermatitis causes intolerable itching, which can cause to insomnia, emotional disturbances, learning disabilities, decreased ability to adapt to the environment, and decreased social activity, etc. It may be also accompanied by severe itching and eczema, which can be mistaken for not keeping skin clean or having infectious skin disease, resulting in poor interpersonal relationships. Especially, in adolescent patients, it can give a negative impact on the development of self-formation. The exact cause of atopic dermatitis has not been known yet. A topical steroid is used as a basic therapeutic agent. However, when it is used for a long period of time, it causes side effects such as skin irritation, being hairy, atrophodermia, hemotelangiosis and steroid acne (Source: National Health Information Portal http://health.mw.go.kr/).

Acne is an inflammatory skin disease that occurs in the face, neck, chest, back, shoulder, etc., with clogged pores (open comedos (or blackheads) and closed comedos (or whiteheads)), pimples, deep boils (cysts or nodules) and the like. It usually starts from puberty (adolescence), and men usually occur between 15 and 19 years, and women between 14 and 16 years. In about 80% of these patients, acne lesions slowly disappear until mid-20s, but occasionally last from 30 to 40 years of age. This is called adult acne. Inflammatory and non-inflammatory lesions appear on the face, body, especially the breast, and the like. It is reported that 8% of the 15-34 year-olds population has acne disease (Source: National Health Information Portal http://health.mw.go.kr/). Acne is not a life-threatening disease, but it puts a psychological burden on the patient. Severe acne has been a cosmetic problem because it can leave a permanent scar if it is not treated seriously and properly. The exact cause of acne is not clear yet, and multiple factors are known to work together (Source: National Health Information Portal http://health.mw.go.kr/). Treatment of acne is generally based on the severity of the symptoms and can be categorized into a broad range of treatments, including vulnerary drugs, oral medications, and surgical treatments (Source: National Health Information Portal http://health.mw.go.kr/). Examples of the vulnerary drug include antibiotics such as clindamycin and erythromycin; vitamin A derivatives such as tretnoin and adapalene, which have an antibacterial function and abilities to ensure good release of sebum together with exfoliation; and benzoyl peroxide, which has a strong antibacterial activity and some anti-inflammatory and clogged pores-melting properties. In recent years, a combination of two or more of these components has been widely used. However, there was little development of therapeutic agents which have few side effects and effective for acne until now.

In addition, psoriasis is characterized by erythematous skin lesions covered with a silvery white squama that has a definite boundary, and it occurs mainly on areas that are highly irritated, such as elbows, knees, hips and scalp. Psoriasis has various clinical manifestations from small papules to platelets, pustulosis, deprived psoriasis, and psoriasis arthritis, etc. It is a chronic inflammatory skin disorder that is repeated with deterioration and improvement in some cases. The cause of psoriasis is not yet known. There are many different methods to treat psoriasis, including localized topical treatments, phototherapy, photodynamic therapy, and recently developed biologic therapy (Source: The Korean Psoriasis Society, http://kspder.or.kr). However, psoriasis is still known to be difficult to cure.

Although the current market for the treatment of inflammatory skin diseases is estimated at about 3 billion US dollars, various folk remedies and biological preparations are used without any specific treatments. Medically, corticosteroids are widely used for oral, topical ointment and nasal spray applications. But there are many limitations to their use due to their serious side effects. A variety of biological preparations are also expensive and limited for general use due to the limited administration methods.

KR Patent registration number 10-1645355, which is related to a skin external preparation for improvement of inflammatory skin diseases, discloses a skin external composition for treating atopic dermatitis comprising an Allium hookeri extract, having excellent antibacterial, antioxidant, moisturizing, and skin barrier properties and an effect of inhibiting expression of inflammatory cytokine.

Ursodeoxycholic acid (UDCA), which is intended to be used for alleviating and treating inflammatory skin diseases in this disclosure, has properties of anti-inflammatory, antioxidant, cell and cell membrane protection, immunomodulatory, mitochondrial protection, and anti-apoptosis in vitro, and the like, so that it will show an excellent efficacy in the treatment of inflammatory skin diseases.

However, in order to be used as an external preparation for skin for the improvement and treatment of inflammatory skin disease and severe pruritus, the problem of skin irritation, which is a major disadvantage of only ursodeoxycholic acid, and the skin impermeability problem must be overcome.

In order to overcome the disadvantages and to achieve a therapeutic effect, the inventors of this disclosure had to firstly dissolve ursodeoxycholic acid at a high concentration in water, which is a raw material of the water-phase layer of the skin application agent. This is because the main factors that need to be improved or innovated in order to increase drug metabolism and pharmacokinetic properties in new drug development are low solubility of the drug candidate substance in water resulting in low permeability.

Ursodeoxycholic acid should be sufficiently dissolved in water at a high concentration, but due to its molecular nature, it has a property that it is practically insoluble in water. Molecular characteristics of ursodeoxycholic acid is that it is a planar amphipathic molecule having both a hydrophobic surface without any substituents and a hydrophilic surface with hydroxyl groups, and it exists in protonated form like other dihydroxy-bile acids.

The maximum solubility of ursodeoxycholic acid in water is as low as 53 μM (20 mg/L). This low solubility is due to the very stable crystal structure of ursodeoxycholic acid molecule. In water, these bile acid anions self-associate themselves in a very narrow range of concentrations to form micelles. The micelles consisting of only the bile acid anions and the accompanying counter ions is called simple micelles, and the main characteristic of the simple bile acid micelles is that it has the ability to be converted into a mixed micelle lipid bilayers.

Therefore, due to the formation of large molecular size of micelles form of bile acid or ursodeoxycholic acid, it is difficult to be pharmacologically active in skin as an independent single molecule. Moreover, because of the molecular size of the micelle, it cannot penetrate well to the skin of the human body. Therefore, there are big disadvantages to exhibit various effects of UDCA. Thus, due to its physicochemical characteristics of its crystalline structure, ursodeoxycholic acid has not been able to penetrate through the skin in an amount effective enough to alleviate or treat dermatosis.

In addition, the acid dissociation constant, pKa, of the crystalline type of ursodeoxycholic acid is about 5.0, which is acidic in water. Thus, there is a serious disadvantage in development of a skin coating agent because it can cause skin irritant when applied to the skin or be harmful when contacted with the skin. That is, this crystalline form of ursodeoxycholic acid has an acicular structure with a very sharp structure, and when applied to the skin, it thus enter into the pores of skin or skin wounds, and since the pH of the skin is acidic, it does not dissolve in this acidic condition and does not wash down, but keeps staying on the spot while constantly irritating the skin to cause skin flare.

In addition, since the crystalline form of ursodeoxycholic acid is well dissolved in ethanol or anhydrous ethanol, it is possible to devise the development of a skin external preparation having an effective concentration for treating inflammatory skin diseases by dissolving ursodeoxycholic acid in a solvent. However, due to the unique chemical nature of ursodeoxycholic acid having both of hydrophilic and hydrophobic surfaces, even though it is dissolved in oil-based (lipophilic) raw material such as ethanol in short-term period, ursodeoxycholic acid molecules are self-associated again to cause micelles or precipitates when the hydrophilic material is added for emulsification in the preparation of a skin application agent. That is, although the crystalline form of ursodeoxycholic acid preparation seems to be temporarily mixed with the oil-based raw material of the skin application agent for a while after dissolving in ethanol, it is not well mixed and emulsified as time passes after feeding oil-based raw materials. Even though the crystalline form of ursodeoxycholic acid is sometimes mixed and emulsified, ursodeoxycholic acid molecules are self-associated again with the elapse of time, which is not suitable for the use as a raw material for manufacturing a skin coating agent because it forms ursodeoxycholic acid micelles or precipitates. As described above, ursodeoxycholic acid (UDCA) is insoluble in water (53 μM) due to its molecular nature and is acidic so it causes skin irritation when applied to skin, and has a fatal disadvantage that it cannot penetrate the skin.

Many researchers in the world have attempted to develop ursodeoxycholic acid for a long period of time to use it as a skin irritant lowering agent. However, it could not be used as a raw material for skin application, since the crystalline form of ursodeoxycholic acid formulation which is sparingly soluble in water is itself classified as skin irritant. There has been no known skin external preparation composition for improving and treating inflammatory skin diseases and severe pruritus containing ursodeoxycholic acid dissolved in water at concentrations as high as 0.15M until now.

SUMMARY

An object of this disclosure is to provide a composition for the prevention or the treatment of inflammatory skin diseases wherein ursodeoxycholic acid is aqueous solubilized in water to be a clear aqueous solution form to use as a skin external preparation which does not cause skin irritation and significantly improves skin permeability of the crystalline ursodeoxycholic acid, which is difficult to penetrate the skin, cause skin irritation, and is harmful to the human body during skin contact.

Another object of this disclosure is to provide an aqueous solubilized ursodeoxycholic acid composition in a clear aqueous solution form to eliminate self-association of ursodeoxycholic acid molecules caused by unique chemical properties of the ursodeoxycholic acid having both hydrophilic and hydrophobic properties at the same time, and to be mixed well with hydrophilic and hydrophobic materials of a skin external preparation and to be emulsified not to form precipitates and self-association even after a long period of time.

Still another object of this disclosure is to provide an aqueous solubilized ursodeoxycholic acid composition which does not cause self-association or precipitates to penetrate the human skin cells with high efficiency and provide pharmacological effect by being present in a single molecule even when the ursodeoxycholic acid is emulsified with raw materials of the composition of a skin external preparation.

Still another object of this disclosure is to provide a clear aqueous solution form of a composition comprising aqueous solubilized ursodeoxycholic acid and maltodextrin as active ingredients for the prevention or the treatment of inflammatory skin diseases which increases skin permeability, reduces discomforts such as skin irritation, and applies the ursodeoxycholic acid to the skin at a high concentration.

Still another object of this disclosure is to provide a skin external preparation for the improvement and the treatment of inflammatory skin diseases comprising the above composition as an active ingredient, which reduces discomforts such as skin irritation after application to the skin.

Still another object of this disclosure is to provide a skin external preparation comprising the above composition as an active ingredient, which has the effect of alleviating symptoms of inflammatory skin diseases.

According to one aspect of this disclosure, there is provided a composition for the prevention or the treatment of inflammatory skin diseases or severe pruritus, the composition comprising active ingredients of: (a) ursodeoxycholic acid (UDCA); (b) an aqueous soluble starch conversion product; and (c) water, wherein the composition is a clear aqueous solution for all pH values.

According to one embodiment of this disclosure, the UDCA described above is an aqueous solubilized UDCA selected from an aqueous soluble UDCA, an aqueous soluble UDCA derivative, a UDCA salt, and a UDCA conjugated with an amine.

According to one embodiment of this disclosure, the UDCA described above is at least one aqueous solubilized UDCA selected from an ursodeoxycholic acid (UDCA), a tauroursodeoxycholic acid (TUDCA) and a glycoursodeoxycholic acid (GUDCA).

According to one embodiment of this disclosure, the UDCA described above is used in an amount of 0.01 to 6 parts by weight based on the total weight of the composition.

According to one embodiment of this disclosure, described above the aqueous soluble starch conversion product is maltodextrin and the maltodextrin is used in an amount of 1.0 to 70 parts by weight based on the total weight of the composition.

According to one embodiment of this disclosure, the pH value described above is from 3 to 9 and the aqueous soluble starch conversion product is a maltodextrin and the minimum weight ratio of the UDCA to the maltodextrin is from 1:16 to 1:30.

According to one embodiment of this disclosure, the pH value described above is from 6 to 9 and an aqueous soluble starch conversion product is a maltodextrin and the minimum weight ratio of the UDCA to the maltodextrin is from 1:13 to 1:30.

According to one embodiment of this disclosure, the aqueous soluble starch conversion product described above is at least one selected from maltodextrin, dextrin, liquid glucose, corn syrup solid, soluble starch, dextran, guar gum, pectin and soluble non-starch polysaccharide.

According to one embodiment of this disclosure, the inflammatory skin diseases described above is one selected from atopic dermatosis, acne, psoriasis, inflammatory skin disease, seborrheic dermatitis and contact dermatitis.

According to one embodiment of this disclosure, the severe pruritus described above includes skin irritation that may cause difficulty in sleep and/or daily life.

According to one embodiment of this disclosure, the UDCA described above is included in an effective amount.

According to an embodiment of this disclosure, the effective amount described above is a quantity capable of preventing or treating inflammatory skin diseases or severe pruritus or of alleviating or treating already generated diseases.

According to another aspect of this disclosure, there is provided a composition for the prevention or the treatment of inflammatory skin diseases or severe pruritus being prepared by drying the composition of this disclosure in powder form.

According to an embodiment of this disclosure, the composition is formulated by mixing the powder described above with water at a pH 7 or lower.

According to still another aspect of this disclosure, there is provided a skin external preparation for the prevention or the treatment of inflammatory skin diseases or severe pruritus comprising the composition described above as an active ingredient.

According to an embodiment of this disclosure, the skin external preparation is formulated into one selected from ointment, gel, cream, patch and spray.

According to an embodiment of this disclosure, the skin external preparation is used once or more a day for one week or longer.

According to still another aspect of this disclosure, there is provided a skin external preparation comprising the composition described above as an active ingredient for alleviating symptoms of burns or inflammatory skin diseases.

According to an embodiment of this disclosure, the skin external preparation described above alleviates at least one symptom of itching, keratinization, and skin irritation caused by inflammatory skin diseases.

According to an embodiment of this disclosure, the skin external preparation is cosmetics.

According to an embodiment of this disclosure, the cosmetics described above is soft toner, astringent toner, nourishing toner, eye cream, nourishing cream, massage cream, cleansing cream, cleansing foam, cleansing water, body lotion, body cream, body essence, shampoo, conditioner, body cleanser, essence or pack.

According to an embodiment of this disclosure, the pH of the skin external preparation described above is from 3 to 9.

The composition for the prevention or the treatment of inflammatory skin diseases or severe pruritus according to one embodiment of this disclosure has an advantage to overcome the skin irritation, which is a fundamental problem of conventional crystalline form of ursodeoxycholic acid, because of a form of ursodeoxycholic acid formulation which is aqueous solubilized in water at a high concentration.

The composition for the prevention or the treatment of inflammatory skin diseases or severe pruritus according to one embodiment of this disclosure has the advantage of achieving an excellent prophylactic or therapeutic effect on inflammatory skin diseases or severe pruritus because of a high permeability to the skin, which enables mass transfer and absorption of ursodeoxycholic acid into skin cells which was impossible due to the limitation of conventional crystalline ursodeoxycholic acid preparations.

The composition for the prevention or the treatment of inflammatory skin diseases or severe pruritus according to one embodiment of this disclosure has an advantage of preventing or treating inflammatory skin diseases even with a small amount because of high skin permeability.

A skin external preparation according to one embodiment of this disclosure can provide a skin external preparation for the prevention or the treatment of inflammatory skin diseases which has little discomfort such as irritation and tingling associated with ursodeoxycholic acid and increases stability of ursodeoxycholic acid preparation.

A skin external preparation according to one embodiment of this disclosure has an advantage to treat acne effectively.

A skin external preparation according to one embodiment of this disclosure has an advantage to suppress excessive sebum secretion, which is one of the causes of acne.

A skin external preparation according to one embodiment of this disclosure has an advantage to effectively treat atopic dermatosis A skin external preparation according to one embodiment of this disclosure has an advantage to effectively treat psoriasis.

A skin external preparation according to one embodiment of this disclosure has an advantage to effectively suppress and treat the inflammatory reaction, which is the main symptom in various inflammatory skin diseases.

A skin external preparation according to one embodiment of this disclosure has an advantage that the moisturizing effect of the conventional skin application agent can be further enhanced.

A skin external preparation according to one embodiment of this disclosure can be provided for the skin external application agent to alleviate symptoms of inflammatory skin diseases or burns.

Thus, the composition and the skin external preparation according to this disclosure have excellent effect in preventing, alleviating, relieving and treating each stage of skin dryness, itching, edema due to local inflammation, hyperkeratosis and microbial infection, etc., which are main clinical features of typical inflammatory skin diseases such as atopic dermatosis, acne, psoriasis, hives, inflammatory skin disease, seborrheic dermatitis and contact dermatitis, and microbial infection, etc.

Other objects and features of this disclosure will become more apparent from the following detailed description, the drawings, and the claims.

BRIEF DESCRIPTION OF THE DRAWINGS

FIG. 7A and FIG. 7B are bar graphs illustrating the changes in acne grade score (A) and improvement rates (%, B) of acne grade score before using a composition, and 2 weeks, 4 weeks, and 8 weeks after using the composition according to one embodiment of this disclosure.

FIG. 12 is a mimetic diagram illustrating an overall test method for evaluating the efficacy in a psoriasis animal model in order to determine the suitability for psoriasis skin according to this disclosure, wherein G1 is a control group in which Vaseline® lotion is applied from day 1 to day 11, G2 is a psoriasis-induced group in which 5% imiquimod (IMQ) cream is applied from day 1 to day 8, and G3 is a group in which 5% imiquimod (IMQ) cream is applied from day 1 to day 8 and simultaneously a test cream from day 5 to day 11 day to determine whether it alleviate or treat psoriasis symptoms.

FIG. 13A is images illustrating the degree of keratinization on the skin of each group on the 10th day, wherein G1 represents "Control+Vaseline Cream (uninduced)," G2 represents "5% IMQ cream only (induced)" and G3 represents "5% IMQ cream (induced)+Test cream. " FIG. 13B is a graph illustrating psoriasis symptoms as disease activity index (DAI). FIG. 13C is a bar graph illustrating the degree of hyperkeratosis on the skin of the psoriasis-induced animal.

DETAILED DESCRIPTION

Figure 1:
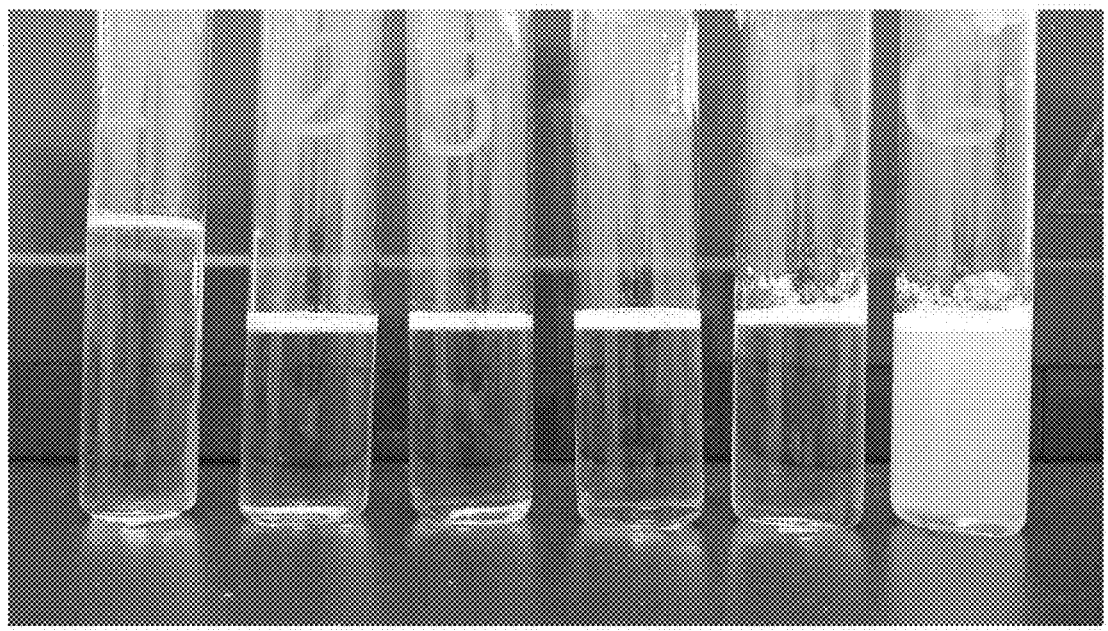
FIG. 1 illustrates whether a clear aqueous solution is formed or not based on pH value of the ursodeoxycholic acid solution prepared in Example 3 of this disclosure.

In order that the disclosure may be more readily understood, certain terms are first defined herein for convenience. Unless otherwise defined herein, the scientific and technical terms used in this disclosure shall have the meaning generally understood by those who are skilled in the art. Unless clearly used otherwise, expressions in the singular number include a plural meaning, and those in the plural number include a singular meaning.

As used herein, the term "treating" or "treatment" encompasses preventing, ameliorating, mitigating and/or managing inflammatory skin diseases and/or conditions by the administration of a composition of this disclosure.

As used herein, the term "comprising as an active ingredient" is meant to contain a certain amount of an active ingredient, enough to provide the effects for, such as prevention, treatment, mitigation of irritation and atopic symptoms, moisturizing and the like as a composition, a skin external preparation composition and a skin external preparation for prevention and treatment of inflammatory skin diseases.

As used herein, the terms "alleviate", "mitigate", or "ameliorate" mean all actions that at least reduce parameters, for example the degree of symptoms, associated with the conditions to be treated.

As used herein, the term "corn syrup" may include both corn syrup and liquid glucose.

The terms "clean aqueous solution" or "clear aqueous solution" used in this disclosure mean a transparent aqueous solution in a solution state in which there are substantially no visually observed precipitates in naked eye.

According to one aspect of this disclosure, there is provided a composition for the prevention or the treatment of inflammatory skin diseases or severe pruritus including active components of: (a) ursodeoxycholic acid (UDCA); (b) an aqueous soluble starch conversion product; and (c) water, wherein the composition is in a clear aqueous solution for all pH values.

As described above, the ursodeoxycholic acid is stabilized with a maltodextrin and as a result, the solubility of pure ursodeoxycholic acid molecules in water can be increased by 3,000 times or more. The aqueous solubilized ursodeoxycholic acid (UDCA), which is dissolved in water by the above method, exists as a nonionic molecular state having amphipathic properties due to its molecular nature, so that the absorption rate of the ursodeoxycholic acid can be drastically increased because it is absorbed in vivo by passive mechanism in addition to high intercellular and intracellular diffusion through fast dispersion by the concentration gradient. All the take together, the aqueous solubilized ursodeoxycholic acid (UDCA), in which an active ingredient of ursodeoxycholic acid is dissolved in water at a high concentration up to 60 g/L, is the most ideal multifunctional anti-inflammatory drug that can prevent, alleviate or treat various kinds of inflammatory skin diseases, pruritus and allergic skin diseases when it is applied as a skin application agent.

UDCA is a non-toxic hydrophilic bile acid, which can be administered orally. The total bile acid content in the human body is as low as about 3%, but it is also present in the bile of the human body. UDCA is the US FDA-approved drug. UDCA can act as an anti-inflammatory agent that can simultaneously control the mRNA expression level of phospholipase A2 and TNF-α producing inflammatory factors, as well as inhibit inflammatory cell damage. The UDCA can be used for cell protection, stabilization/protection of cell membrane in a dose-dependent manner, anti-apoptotic effect in a dose-dependent manner, immune modulating effect by the activation of intracellular glucocorticoid receptor in a dose-dependent manner, inhibition of TNF-α expression and anti-inflammatory effects by inhibition of induction of nitric oxide synthase (Hepatology Research 2008; 38: 123-131).

The composition of this disclosure may include, but is not limited to, the solubility of UDCA in the composition can be about 3,000 times higher than the conventional commercialized UDCA preparation (0.15 M vs. 0.05 mM) and can be about 300 times or much higher compared to the taurine conjugate form of ursodeoxycholic acid (TUDCA). The solubility of UDCA in the protonated form is about 0.05 mM and the solubility of TUDCA is 0.45 mM and the TUDCA has relatively low solubility when it is protonated but is about 10 times higher than the solubility of the commercialized UDCA (pH 1 to 8). Accordingly, this disclosure includes UDCA and TUDCA.

When UDCA is administered orally, about 30 to 60% of it is absorbed along the jejunum and ileum by nonionic passive diffusion and the crystalline structure of UDCA (crystalline form of UDCA), due to insolubility, is absorbed only by a small amount (up to 20% of intakes) at the ileum of the colon by the active transport mechanism. When UDCA is absorbed by hepatocytes, it can be conjugated with taurine and glycine, and thus synthesized TUDCA and GUDCA are excreted by hepatic first-pass clearance as bile acids secreted from the human body. Therefore, the concentration of UDCA in the blood after oral administration is very low, which is insufficient for an effective amount for the treatment of skin diseases. Thus, a large amount of dose is required in order to provide a composition for the prevention or the treatment of inflammatory diseases.

However, since the composition of this disclosure has higher skin permeability of UDCA in an aqueous solution and completely dissolves the UDCA in the formulation of this disclosure as compared with the conventional oral dosage form and powder formulations (form achievable by the conventional formulations in which the bile is incompletely solubilized), it is possible to achieve high preventive or therapeutic effects against inflammatory skin diseases even with administration of a low dose.

The manufacturing method according to this disclosure can be used to prepare aqueous solution formulations with a high molecular weight aqueous soluble starch conversion products [e.g., Maltrin M150 (DE=15), Maltrin M180 (DE=18), Maltrin M200 (DE=20), Maltrin M250 (corn syrup: DE=25, liquid glucose)] or a soluble non-starch polysaccharides (e.g., guar gum, pectin, arabic gum) having various concentrations of bile acids (salts) and their corresponding minimum amount of dextrose equivalent (DE) ranging from 15 to 25

According to one embodiment of this disclosure, the ursodeoxycholic acid which is selected from an aqueous soluble ursodeoxycholic acid, an aqueous soluble ursodeoxycholic acid derivative, an ursodeoxycholic acid salt, and an ursodeoxycholic acid conjugated with an amine can be aqueous solubilized ursodeoxycholic acid. An aqueous soluble metal salt of ursodeoxycholic acid, an inclusion complex between ursodeoxycholic acid and cyclodextrin and a derivative thereof, and an aqueous soluble O-sulfonated bile acid are also included as an aqueous soluble ursodeoxycholic acid salt.

According to one embodiment of this disclosure, the ursodeoxycholic acid may be at least one aqueous solubilized UDCA selected from an ursodeoxycholic acid (UDCA), a tauroursodeoxycholic acid (TUDCA) and a glycoursodeoxycholic acid (GUDCA).

According to one embodiment of the disclosure, there is provided a composition for preventing or treating inflammatory skin disease or severe pruritus, which comprises 0.01 to 6 parts by weight of ursodeoxycholic acid based on the total weight of the composition. However, it is not limited thereto.

If the amount of ursodeoxycholic acid is less than 0.01 part by weight based on the total weight of the composition, the effects for the prevention or the treatment of inflammatory skin diseases or severe pruritus may be insignificant. On the other hand, if the amount of ursodeoxycholic acid is more than 6 parts by weight, a clear aqueous solution may not be formed. When cloudy precipitates are formed instead of a clear aqueous solution, it may be difficult to use it as a skin application agent.

When precipitates are formed, ursodeoxycholic acid may not be dissolved in water and thus exist in a crystalline form of UDCA. When this is used for preparing a skin application agent, it may cause skin irritation due to the crystalline form of UDCA. Thus the preparation of a clear aqueous solution is required to remove all of the crystalline form of UDCA that can cause skin irritation.

According to one embodiment of this disclosure, there is provided a composition for preventing or treating inflammatory skin disease or severe pruritus, wherein the aqueous soluble starch conversion product is maltodextrin, and the maltodextrin is used in an amount of 1.0 to 70 parts by weight based on the total weight of the composition. However, it is not limited thereto.

When the amount of maltodextrin is less than 1.0 part by weight, an effective amount of UDCA cannot be dissolved in water, resulting in poor effects for the prevention or the treatment of inflammatory skin diseases or severe pruritus. On the other hand, when the amount of maltodextrin is more than 70 parts by weight, precipitates are formed, resulting in skin irritation since UDCA or maltodextrin precipitates out of the aqueous solution.

According to one embodiment of this disclosure, an aqueous soluble starch conversion product is maltodextrin, and the minimum weight ratio of maltodextrin to the ursodeoxycholic acid may be 1:30, including but not limited to 1:25, 1:20, 1:15, 1:12, or 1:6. An amount of the aqueous soluble starch conversion product with high molecular weight used in the composition can be defined as an aqueous solubilized amount of the selected ursodeoxycholic acid at a desired concentration and the pH range described herein. The minimum amount of maltodextrin may be equally applied to the case of tauroursodeoxycholic acid and glycoursodeoxycholic acid.

According to one embodiment of this disclosure, there is provided a composition for preventing or treating inflammatory skin disease or severe pruritus, wherein the pH value is from 3 to 9 and an aqueous soluble starch conversion product is maltodextrin, wherein the minimum weight ratio of UDCA to maltodextrin is 1:16-1:30. The minimum weight ratio of UDCA to maltodextrin may be 1:16-1:20, 1:16-1:25, 1:16-1:30, 1:20-1:25, 1:20-1:30, or 1:25-1:30. However, it is not limited thereto.

When the pH value is from 3 or higher to less than 6 and the minimum weight ratio of UDCA to maltodextrin is 1:1-1:15, precipitates may be formed, resulting in no clear aqueous solution.

According to one embodiment of this disclosure, there is provided a composition for preventing or treating inflammatory skin disease or severe pruritus, wherein the pH value is 6 to 9, the aqueous soluble starch conversion product is maltodextrin, and the minimum weight ratio of UDCA to maltodextrin is 1:13-1:30. However, it is not limited thereto.

The aqueous soluble starch conversion product of this disclosure comprises a carbohydrate obtained directly from partial or incomplete hydrolysis of starch under various pH conditions. Non-limiting examples of the aqueous soluble starch conversion product may include maltodextrin, dextrin, liquid glucose, corn syrup solid (dried powder of liquid glucose). The corn syrup solid may be Maltrin M200 and the maltodextrin may be Maltrin M700, both of which are manufactured by GPC™ (Grain Processing Corporation) of Muscatin, Iowa, USA. However, it is not limited thereto.

If the starch conversion product consists of a polymer, the polymer may include at least one reducing end and at least one non-reducing end and may be linear or branched. The molecular weight may be about 100 mass units or more, or 106 mass units or more. The high molecular weight aqueous soluble starch conversion product, though not limited thereto, may have a molecular weight of 105 mass units or more.

According to one embodiment of this disclosure, the composition may further include a soluble non-starch polysaccharide. The soluble non-starch polysaccharide may be obtained under various pH conditions by various hydrolysis or synthesis mechanisms. Non-limiting examples of the soluble non-starch polysaccharide include dextran, guar gum, pectin, indigestible soluble fibers, and the like. If the soluble non-starch polysaccharide is composed of a polymer, the polymer may have at least one reducing end and at least one non-reducing end. The polymer described above may be a linear or branched. The molecular weight of the polysaccharide of this disclosure may be at least about 100 mass units, or at least about 106 mass units, preferably at least 105 mass units. However, it is not limited thereto. The composition may be provided as a composition which is an aqueous solution comprising a combination of the aqueous soluble starch conversion product and/or the aqueous soluble non-starch polysaccharide.

According to one embodiment of this disclosure, the minimum weight ratio of ursodeoxycholic acid to liquid glucose (e.g., corn syrup) needed to prevent precipitation of the composition is about 1:25 (i.e., about 12.5 g per 500 mg of ursodeoxycholic acid in 100 ml of water or about 25 g per 1 g of ursodeoxycholic acid in 200 ml of water). However, it is not limited thereto.

In addition, the minimum amount of dried powder of liquid glucose (corn syrup solids, e.g., Maltrin M200) to ursodeoxycholic acid needed to prevent precipitation of the composition from the dosage form of this disclosure is about 30 g per 1 g of ursodeoxycholic acid in 100 ml of water, or about 60 g per 2 g of ursodeoxycholic acid in 200 ml of water. However, it is not limited thereto.

The minimum amount of the soluble non-starch polysaccharide required to prevent precipitation of the composition from the dosage form according to one embodiment of this disclosure is about 50 g of guar gum per 500 mg of ursodeoxycholic acid in 100 ml of water, or 80 g of pectin per 500 mg of ursodeoxycholic acid in 100 ml of water. However, the minimum required amount of the soluble non-starch polysaccharide or aqueous soluble starch conversion product with high molecular weight may be determined mainly by the absolute amount of ursodeoxycholic acid in the solution preparation rather than the concentration.

The composition of this disclosure may further include dietary fiber. Non-limiting examples of the dietary fiber include guar gum, pectin, psyllium, oat rubber, soybean fiber, oat bran, corn hull, cellulose, and wheat bran.

The composition of this disclosure may further comprise an emulsifying agent and a suspending agent. Non-limiting examples of the emulsifying agent include guar gum, pectin, acacia, carrageenan, sodium carboxymethylcellulose, hydroxymethylcellulose, hydroxypropylcellulose, methylcellulose, polyvinylalcohol, povidone, tragacanth gum, xanthan gum and sorbitan ester.

The composition of this disclosure may further include a pharmaceutically acceptable additive. Examples of the pharmaceutically acceptable additive include starch, gelatinized starch, microcrystalline cellulose, lactose, povidone, colloidal silicon dioxide, calcium hydrogenphosphate, lactose, mannitol, glutinous, arabic gum, pregelatinized starch, corn starch, powder cellulose, hydroxypropylcellulose, opadry, sodium starch glycolate, carnauba wax, synthetic aluminum silicate, stearic acid, magnesium stearate, aluminum stearate, calcium stearate, white sugar, dextrose, sorbitol and talc. The pharmaceutically acceptable additive according to this disclosure is preferably included in the composition in an amount of 0.1 to 90 parts by weight. However, it is not limited thereto.

In addition, the composition of this disclosure may be administered as an external preparation for skin at the time of actual clinical administration. In the case of formulation, a diluent or excipient such as a filler, an extender, a binder, a wetting agent, and a surfactant may be added.

According to one embodiment of this disclosure, there is provided a composition for preventing or treating inflammatory skin diseases, wherein the pH of the aqueous solubilized ursodeoxycholic acid composition is in the range of 3 to 9, and wherein the composition is in a stable aqueous solution state without visual precipitation at the pH value. The composition describe above may be solubilized in water and may be in the form of an aqueous solution without precipitation at the pH described above. A selected pH range that does not precipitate the ursodeoxycholic acid and the aqueous soluble starch conversion product in the composition may be from about pH 1 to about pH 10, preferably from about pH 3 to about pH 9, more preferably from pH 6 to pH 9, and most preferably from pH 6.5 to pH 7.5. In addition, it may contain acids, bases and buffering agent if necessary to maintain the pH describe above. The pH adjusting material may be, but is not limited to, HCl, $H_3PO_4$, $H_2SO_4$, $HNO_3$, $CH_3COOH$, citric acid, malic acid, tartaric acid, lactic acid, phosphate, eidetic acid and alkali. The properties and methods for using such pH adjusting materials are well known in the art. The pH range is the pH level of any subset that can be obtained in an aqueous system sufficient to allow various formulations to remain in solution from the preparation and to be applied to the skin to be absorbed, depending on the method of administration. Thus, the composition may be used as a formulation in solution, without the composition according to this disclosure being precipitated at the pH level of the skin. According to some embodiments of this disclosure, ursodeoxycholic acid remains dissolved under acidic conditions as a free ursodeoxycholic acid even though it is generally insoluble under acidic conditions. The composition described above may further include another composition in which the composition remains soluble when added to a skin application formulation. In addition, the composition may provide a clear and stable solution for providing a composition for the prevention or the treatment of inflammatory skin diseases or severe pruritus.

According to one embodiment of this disclosure, there is provided a composition for preventing or treating the inflammatory skin disease wherein the inflammatory skin disease is selected from atopic dermatosis, acne, psoriasis, hives, inflammatory skin disease, seborrheic dermatitis and contact dermatitis.

The hives (urticaria) is a common skin disease when permeability of blood vessels existing in the skin or mucous membranes is increased to temporarily accumulate plasma components in the tissues, resulting in reddening of skin, swelling of white, and severe itching. Hives is often accompanied by skin swollen due to partial edema of the upper level of skin, and severe itching or tingling. The swelling of the skin is called wheal, as when it is bitten by an insect. Hives is characterized by a variety of sizes of wheals surrounded by red rashes. Angioedema is similar to hives, but the swelling occurs beneath the skin instead of on the surface. Hives or angioedema is a common disease that has a lifetime prevalence of about 20%. Hives is divided into acute and chronic hives/angioedema according to the period. Acute hives is usually caused by food or drug, and is usually gone within 6 weeks, and chronic hives lasts more than 6 weeks. It is often impossible to find out exactly why hives has formed. It is reported that the cause of hives cannot be found in 50% of people with acute hives and 70% of people with chronic hives (Seoul National University Hospital Medical Information).

Inflammatory skin disease is not limited to this, and it refers to symptoms that are caused by inflammation among skin diseases, but parasites, microorganisms, allergies, etc. cannot be considered as a cause (Agricultural dictionary published by Rural Development Administration of Korea).

Seborrheic dermatitis is a kind of long-lasting eczema. It is a chronic inflammatory skin disease that occurs mainly in the scalp and face, especially around eyebrows, nose, lips, ears, armpits, chest, inguinal region and the like where sebum secretion occurs vigorously due to increased activity of the sebaceous glands. The causes of seborrheic dermatitis are related to the theory that sebum is involved directly or indirectly in the development of the disease, the theory that it is caused by bacteria and yeast, the theory that it is related to the neurotransmitter abnormality, and the theory that it is seasonal change or epidermal hyperplasia. However, the specific causes are not known. Seborrheic dermatitis occurs most common in those less than 3 months old and those between 40 and 70 years old. Babies are affected regardless of sex, but in adults males are more often affected than females. Seborrheic dermatitis is related with oily skin. It is characterized by dry or greasy yellow scales (squama) on the erythema and may be accompanied by itching. It may appear on a whole body with recurring improvement and deterioration but may appear as a localized rash. Seborrheic dermatitis may also cause flaking in the scalp which is known as dandruff. In case of seborrheic dermatitis in face, papulose rash (less than 1 cm in size) may occur on the cheeks, nose and forehead. Redness and flaking may also occur near the eyebrow and the skin under the scales is reddish. Sometimes the eyelids are yellowish red and sometimes covered with fine scales. Seborrheic dermatitis occurred on ears may cause flaky scales and severe itching. It may appear behind the ears and under the earlobe. In the armpit area, the rash starts from the nipple and spreads bilaterally to the surrounding skin, so it looks like allergic contact dermatitis by a deodorant. Scales in the groin area and between the buttocks are very fine, the boundaries are less clear, and it tends to be bilateral and symmetrical. Cracks may occur in areas where skin overlaps (Seoul National University Hospital Medical Information).

Contact dermatitis is caused by the contact with a foreign substance. It is classified into primary contact dermatitis caused by irritation of a contact substance itself and allergic contact dermatitis caused only in a person having an allergic reaction to a contact substance. Contact dermatitis is divided into irritant contact dermatitis and allergic contact dermatitis, but symptoms are similar from each other. Symptoms of both forms include eczematous lesions accompanied by erythema (round red dot) and edema. In some cases, acne lesions, hives lesions, multiform erythema, pigmentation, and granulomatous lesions may also occur (Seoul National University Hospital Medical Information).

In the case of psoriasis or atopic dermatosis, the roughness of skin appears as keratinization or abnormal formation of keratinocytes formed with stratum corneum increases. The composition of this disclosure can be used for the alleviation and treatment of hyperproliferative skin disorders by controlling proliferation rate of theses keratinocytes.

According to one embodiment of this disclosure, there is provided a composition for preventing or treating inflammatory skin disease or severe pruritus, wherein the skin pruritus causes difficulty in normal activities due to the irritation to sleep and daily life.

According to one embodiment of this disclosure, there is provided a composition for the prevention or the treatment of inflammatory skin diseases or severe pruritus, wherein the aqueous solubilized ursodeoxycholic acid is contained in an effective amount.

In this disclosure, the effective amount means an amount capable of preventing or treating an inflammatory skin disease or severe pruritus, or alleviating or treating an already-generated disease, and includes a therapeutically active amount. The effective amount may vary depending on the form of being commercialized, the method applied to the skin, and the time of staying on the skin. For example, when the composition is commercialized as a skin external preparation for the improvement or the treatment for skin diseases or severe pruritus, the daily dosage may be 0.1 to 100 mg/kg based on ursodeoxycholic acid, preferably 30 to 80 mg/kg, more preferably 50 to 60 mg/kg. It may be used 1 to 6 times a day.

The effective amount described above may be generally 0.001 to 1.5 parts by weight, preferably 0.005 to 1.0 parts by weight, and more preferably 0.01 to 0.5 parts by weight, based on the entire skin application agent composition.

According to one embodiment of this disclosure, the composition may be dried and formulated in powder form. The composition in powder form may be easy to store or handle and has an advantage of being easy to manufacture a composition of a desired form of preparation.

According to one embodiment of this disclosure, the powder may be mixed with water at pH 7 or lower to prepare a liquid form. The composition in powder form may be mixed with weak acid and neutral condition as well as water, which is advantageous in manufacturing a composition of a desired preparation.

According to another aspect of this disclosure, there is provided a skin external preparation for the prevention or the treatment of inflammatory skin diseases or severe pruritus comprising the aqueous solubilized ursodeoxycholic acid as an active ingredient.

The skin external preparation including the composition maintains the state in which no self-association of ursodeoxycholic acid molecules occurs (the state in which no micelles are formed) at the above-mentioned pH. The selected pH range in which the compounds are not self-associated is from about pH 3 to about pH 9, but is not limited thereto, preferably from pH 4.5 to pH 8, and more preferably from pH 6 to pH 7. In addition, it may contain acids, bases and buffering agents if necessary to maintain the pH.

The skin external preparation described above may contain at least one of Carbopol #941 (1%), EDTA-2Na, Nipagin M (M-P), DL-panthenol, 1,3-B.G, Nipasol M (P-P), Vit. E. Acetate, Tween #60, Arlacel #60, Arlacel #165, GMS105, Kalcol6850, stearic acid, CEH, macadamia nut oil, Lily 70, TCG-M, KF-96A, (6cs), KF 995, DC200f100cs, T.E.A, Sepigel305, bacillus/bean/folic acid fermented extract, *Morus alba* bark extract, *Artemisia vulgaris* extract, *Citrus grandis* seed extract, *Portulaca oleracea* extract, *Hippophae rhamnoides* fruit extract, *Cacao* extract, *Chamomilla recutita* flower extract, *Propolis* extract, silver ear fungus extract, *Guajava* leaf extract, *Camellia sinensis* leaf extract, witch hazel extract, *Rosa damascena* flower extract, *Salix alba*(willow) bark extract, honey extract and royal jelly extract, marine collagen. It may further contain trace amounts of preservatives, fragrances, pigments and purified water, if necessary.

When the extract is used, it has excellent antimicrobial, anti-inflammatory and moisturizing properties. For example, in the case of silver ear fungus extract, it forms a moisture protective film and has a high moisture retention ability. *Artemisia vulgaris* extract may have a skin soothing effect and the like. In addition, a synergistic effect may be obtained when the above extract is added to the composition in a specific combination.

In addition to the aqueous solubilized ursodeoxycholic acid in a clear aqueous solution, the skin external preparation according to this disclosure may further include a lipid, an organic solvent, a solubilizing agent, a gelling agent, a softening agent, an antioxidant, a suspending agent, a stabilizer, a foaming agent, surfactant, water, an ionic or non-ionic emulsifier, a filler, a sequestering agent and a chelating agent, a preservative, a vitamin, a blocking agent, a wetting agent, a skin sealant, a ceramide-containing moisturizer, an essential oil, a dye, a pigment, a hydrophilic or lipophilic active agent, an adjuvant commonly used in the field of dermatology, such as any other ingredient conventionally used in skin application agents. The above ingredients may be contained in amounts commonly used in the field of dermatology.

According to one embodiment of this disclosure, there is provided a skin external preparation for the prevention or the treatment of inflammatory skin disease or severe pruritus, wherein the composition is selected from ointment, gel, cream, patch, powder and spray. The skin external preparation of this disclosure may be formulated in any preparation conventionally produced in the art and may be in the form of solution, suspension, emulsion, paste, soap, surfactant-containing cleansing, oil, foundation, emulsion foundation, wax foundation, or spray, but is not limited thereto.

When it is formulated in the form of spray agent, the skin external preparation of this disclosure may include lactose, talc, silica, aluminum hydroxide, calcium silicate or polyamide powder as carrier component. Particularly, in the case of a spry, it may further include a propellant such as chlorofluorohydrocarbon, propane/butane or dimethyl ether.

When it is formulated in the form of solution or emulsion, the skin external preparation of this disclosure may include a solvent, a solubilizing agent or an emulsifying agent as a carrier component, and examples therefore include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol or sorbitan fatty acid ester.

When it is formulated in the form of suspension, the skin external preparation of this disclosure may use, as a carrier component, a liquid diluent such as water, ethanol or propylene glycol, a suspending agent such as ethoxylated isostearyl alcohol, polyoxyethylene sorbitol ester and polyoxyethylene sorbitan ester, crystallite cellulose, aluminum metahydroxide, bentonite, agar or tragacanth When it is formulated in the form of surfactant-containing cleansing, the skin external preparation of this disclosure may include, as a carrier component, aliphatic alcohol sulfate, aliphatic alcohol ether sulfate, sulfosuccinic acid monoester, isethionate, imidazolinium derivative, methyltaurate, sarcosinate, fatty acid amide ether sulfate, alkylamidobetaine, aliphatic alcohol, fatty acid glyceride, fatty acid diethanolamide, vegetable oil, lanolin derivative or ethoxylated glycerol fatty acid ester.

The skin application agent composition including the aqueous solubilized ursodeoxycholic acid in a clear aqueous solution may be preferably formulated in the form of cream. The cream includes a W/O type such as cold cream and emollient cream and an O/W type such as shaving cream, varnish cream, hand cream, and rinsing cream. Preferably, the cream is vanishing cream typically containing water and stearic acid. Usually, patients or doctors prefer cream rather than ointment because the O/W cream is easier to wash out than ointment. From this point of view, cream is preferable as a composition formulation of this disclosure.

The skin application agent composition including the aqueous solubilized ursodeoxycholic acid in a clear aqueous solution may be preferably formulated in the form of lotion. The lotion is prepared by methods such as suspension, emulsion, liquid and the like, which also belong to the ordinary skill in the art of pharmaceutical formulation. Preferably, the lotion is a white lotion which can also be prepared by those skilled in the art of formulation.

The skin application agent composition including the aqueous solubilized ursodeoxycholic acid in a clear aqueous solution may be also preferably formulated in the form of liniment. The liniment may be oil liniment or ethanolic liniment, more preferably oil liniment which is less irritating to the skin. The oil liniment may include a nonvolatile oil such as almond oil, peanut oil, cottonseed oil and the like, or a volatile oil such as wintergreen, turpentine and the like.

Each effective amount for alleviating or treating inflammatory skin diseases and severe pruritus dermatitis may vary with the severity of the underlying disease and the type of formulation. In addition, the number of times of application may vary depending on the age, body weight, and constitution of the patient.

According to one embodiment of this disclosure, the skin external preparation for the prevention or the treatment of inflammatory skin disease or severe pruritus having a formulation of cream may be provided.

When it is formulated in the form of cream, paste or gel, the skin external preparation described above may include animal oil, vegetable oil, wax, paraffin, starch, tragacanth, cellulose derivative, polyethylene glycol, silicone, bentonite, silica, talc or zinc oxide as a carrier component. Formulations of the disclosure may act as a carrier, an adjuvant or enhancer for the delivery of a pharmaceutical material which remains dissolved in the composition of the disclosure over the desired pH range. The skin external preparation may further include, but is not limited to, an incompletely soluble non-bile acid drug.

According to one embodiment of this disclosure, there is provided a skin external preparation for preventing or ameliorating an inflammatory skin disease or severe pruritus, which is characterized by being used for at least one week and at least once a day.

Figure 7A:
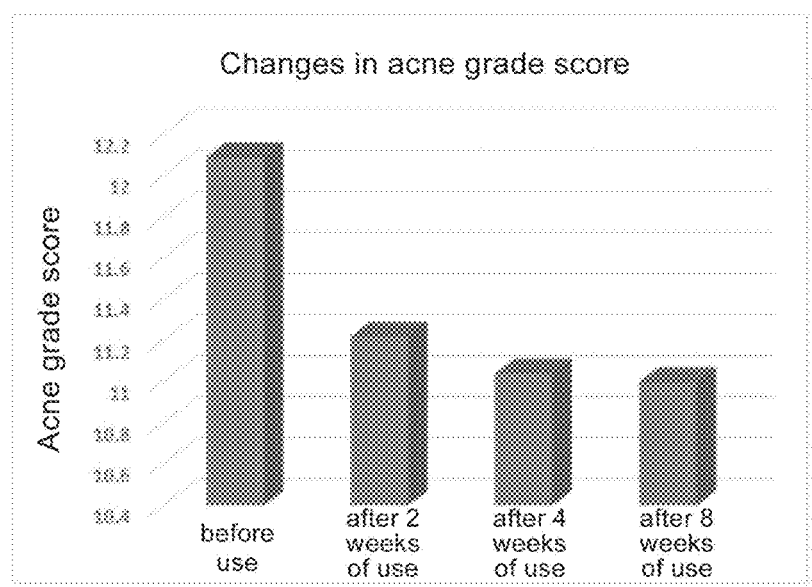

Experimental results of the Experimental Examples of this disclosure and FIG. 7 to FIG. 9 show that the effect of skin external preparation according to this disclosure was apparently exhibited after 2 weeks from a subject having acne dermatosis.

According to another aspect of this disclosure, there is provided a skin external preparation characterized in that the composition alleviates symptoms due to burn or inflammatory skin diseases.

Methods and dosages for administration of the compositions of this disclosure may be designed to any measure to prevent and/or treat subjects of varying ages, additional allergies or diseases and different severity of symptoms. The method of administration and dosage may be adapted to variations over time. Those which are the same as or can be substituted for obvious changes and modifications may be included within the scope of this disclosure. Thus, those skilled in the art will understand that there is no intention to limit this disclosure by a single embodiment, use, and/or advantage from other embodiments.

This disclosure contains extensive information on the current awareness of the genetics, biochemistry, and cell biology of inflammatory skin diseases, but future research may reveal that aspects of these perceptions are either inaccurate or incomplete. Thus, those skilled in the art will understand that this disclosure is not limited to a particular model or mechanism of action whether part of this disclosure is taken or not.

In addition, those skilled in the art will recognize that other equivalent or alternative compositions and methods may be utilized. For example, although it has been described that a plurality of compounds can be administered together with ursodeoxycholic acid, it is understood that other compounds may also be included.

Also, the application of another drug may be performed at the same time as the administration of the aqueous solubilized ursodeoxycholic acid composition of this disclosure, or they may be administered separately in the same or overlapped time period (for example, at the same time, the same date, or the same week).

According to one embodiment of this disclosure, the skin external preparation may be cosmetics. The cosmetics may be selected from soft toner, astringent toner, nourishing toner, eye cream, nourishing cream, massage cream, cleansing cream, cleansing foam, cleansing water, body lotion, body cream, body essence, shampoo, conditioner, body cleanser, essence and pack. The cosmetics may also be one selected from skin lotion, toner, softener, astringent, lotion, milky lotion, moisturizing lotion, nourishing lotion, hand cream, nourishing essence, soap, cleansing cream, emulsion, eye shadow and the like. However, it is not limited thereto.

In addition to the aqueous solubilized ursodeoxycholic acid, the cosmetic composition according to this disclosure may further include one or more of a lipid, an organic solvent, a solubilizing agent, a gelling agent, a softening agent, an antioxidant, a suspending agent, a stabilizer, a foaming agent, a flavoring agent, a surfactant, water, an ionic or non-ionic emulsifier, a filler, a sequestering agent and a chelating agent, a preservative, a vitamin, a blocking agent, a wetting agent, a skin sealant, a ceramide-containing moisturizer, an essential oil, a dye, a pigment, a hydrophilic or lipophilic active agent, an adjuvant commonly used in the field of dermatology, such as any other ingredient commonly used in a lipid vesicle or skin application agent. The above ingredients may be included in an amount commonly used in the field of cosmetic science or dermatology.

According to one embodiment of this disclosure, the pH of the skin external preparation is from 3 to 9.

Hereinafter, this disclosure will be described in more detail with the following examples.

EXAMPLES

Example 1. Preparation of an Aqueous Solubilized ursodeoxycholic Acid in a Clear Aqueous Solution A clear aqueous stock solution of aqueous solubilized ursodeoxycholic acid, containing natural ursodeoxycholic acid (UDCA) and aqueous soluble starch with low glucose equivalent, was prepared.

Specifically, 6.7 g of sodium hydroxide pellets were dissolved in 400 ml of purified water. 60 g of ursodeoxycholic acid was dissolved in the sodium hydroxide solution under stirring at room temperature. 360 g of maltodextrin was added to the clear solution little by little and stirred. A preservative was then added in an amount appropriate for the pharmaceutical formulation to the clear solution obtained by performing ultrasonication (750W, 20 kHz) at high throughput and the pH was adjusted by the dropwise addition of HCl. Purified water was added and adjusted to be a total of 1,000 ml. If necessary, the clear solution was filtered with a suitable filtration apparatus. This filtration is important for removing impurities from the raw material or sterilization, but it is not intended to remove the granular material because the solution is already clear. As shown in Table 1, the prepared ursodeoxycholic acid solution formed a clear aqueous solution at pH 10.3, 9.2, and 6.7 without visual precipitation, but formed precipitates at pH 5.4.

Example 2. Preparation of an Aqueous Solubilized ursodeoxycholic Acid in a Clear Aqueous Solution A clear aqueous stock solution of aqueous solubilized ursodeoxycholic acid, containing natural ursodeoxycholic acid (UDCA) and aqueous soluble starch with low glucose equivalent, was prepared.

Specifically, it was prepared in accordance with the same procedure as in Example 1, except that 720 g of maltodextrin as one high molecular weight aqueous soluble starch conversion product per 60 g of ursodeoxycholic acid was used. As shown in Table 1, the prepared ursodeoxycholic acid solution formed a clear aqueous solution at pH 9.6, 7.3, 6.5 and 6.0 without any visible precipitation, but formed precipitates at pH 5.5.

Example 3. Preparation of an Aqueous Solubilized ursodeoxycholic Acid in a Clear Aqueous Solution A clear aqueous stock solution of aqueous solubilized ursodeoxycholic acid, containing natural ursodeoxycholic acid (UDCA) and aqueous soluble starch with low glucose equivalent, was prepared.

Specifically, it was prepared in accordance with the same procedure as in Example 1, except that 750 g of maltodextrin as one high molecular weight aqueous soluble starch conversion product per 50 g of ursodeoxycholic acid was used. 5.7 g of sodium hydroxide pellets were dissolved in 400 ml of purified water and then used. As shown in Table 1, the prepared ursodeoxycholic acid solution formed a clear aqueous solution at pH 9.5, 8.9, 7.9, 7.1, and 6.0 without visual precipitation, but formed precipitates at pH 5.5. FIG. 1 is images illustrating whether a clear aqueous solution of the ursodeoxycholic acid solution is formed or not at each pH value.

Example 4. Preparation of an Aqueous Solubilized ursodeoxycholic Acid in a Clear Aqueous Solution A clear aqueous stock solution of aqueous solubilized ursodeoxycholic acid, containing natural ursodeoxycholic acid (UDCA) and aqueous soluble starch with low glucose equivalent, was prepared.

Figure 2:
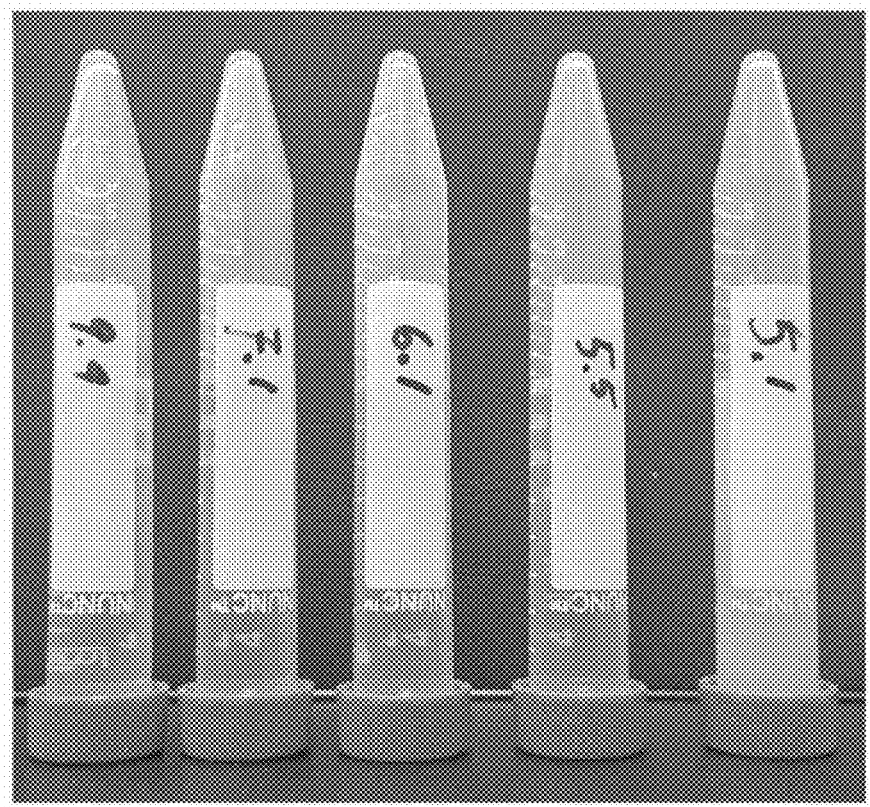
FIG. 2 illustrates whether a clear aqueous solution is formed or not based on pH value of the ursodeoxycholic acid solution prepared in Example 4 of this disclosure.

Specifically, it was prepared in accordance with the same procedure as in Example 1, except that 350 g of maltodextrin as one high molecular weight aqueous soluble starch conversion product per 17.5 g of ursodeoxycholic acid was used. 2.0 g of sodium hydroxide pellets were dissolved in 400 ml of purified water and then used. As shown in Table 1, the prepared ursodeoxycholic acid solution formed a clear aqueous solution at pH 9.4, 7.1, 6.1, and 5.5 without visual precipitation, but formed precipitates at pH 5.1. FIG. 2 is images illustrating whether a clear aqueous solution of the ursodeoxycholic acid solution is formed or not at each pH value.

Example 5. Preparation of an Aqueous Solubilized ursodeoxycholic Acid in a Clear Aqueous Solution A clear aqueous stock solution of aqueous solubilized ursodeoxycholic acid, containing natural ursodeoxycholic acid (UDCA) and aqueous soluble starch with low glucose equivalent, was prepared.

Figure 3:
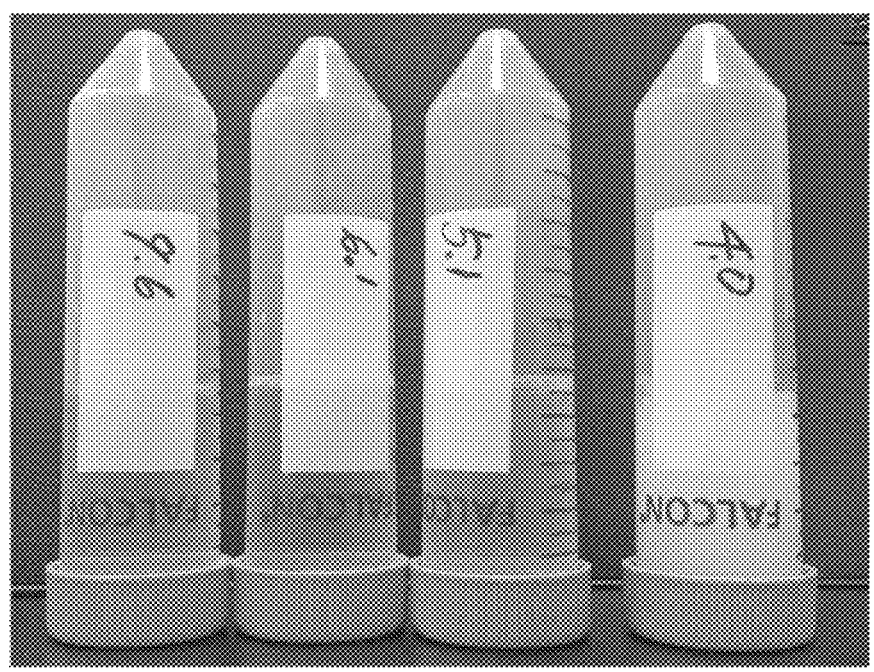
FIG. 3 illustrates whether a clear aqueous solution is formed or not based on pH value of the ursodeoxycholic acid solution prepared in Example 5 of this disclosure.

Specifically, it was prepared in accordance with the same procedure as in Example 1, except that 350 g of maltodextrin as one high molecular weight aqueous soluble starch conversion product per 14 g of ursodeoxycholic acid was used. 1.7 g of sodium hydroxide pellets were dissolved in 400 ml of purified water and then used. As shown in Table 1, the prepared ursodeoxycholic acid solution formed a clear aqueous solution at pH 9.6, 6.1, and 5.1 without visual precipitation, but formed precipitates at pH 4.0. FIG. 3 is images illustrating whether a clear aqueous solution of the ursodeoxycholic acid solution is formed or not at each pH value.

Example 6. Preparation of an Aqueous Solubilized ursodeoxycholic Acid in a Clear Aqueous Solution A clear aqueous stock solution of aqueous solubilized ursodeoxycholic acid, containing natural ursodeoxycholic acid (UDCA) and aqueous soluble starch with low glucose equivalent, was prepared.

Figure 4:
FIG. 4 illustrates whether a clear aqueous solution is formed or not based on pH value of the ursodeoxycholic acid solution prepared in Example 6 of this disclosure is formed or not based on pH value.

Specifically, it was prepared in accordance with the same procedure as in Example 1, except that 750 g of maltodextrin as one high molecular weight aqueous soluble starch conversion product per 25 g of ursodeoxycholic acid was used. 2.8 g of sodium hydroxide pellets were dissolved in 400 ml of purified water and then used. As shown in Table 1, the prepared ursodeoxycholic acid solution formed a clear aqueous solution at pH 9.0, 8.0, 7.0, 6.0, 5.1, 4.1, 2.9 without visual precipitation. FIG. 4 is images illustrating whether a clear aqueous solution of the ursodeoxycholic acid solution is formed or not at each pH value.

Example 7. Preparation of an Aqueous Solubilized ursodeoxycholic Acid in a Clear Aqueous Solution A clear aqueous stock solution of aqueous solubilized ursodeoxycholic acid, containing ursodeoxycholic acid and ursodeoxycholic acid derivative and aqueous soluble starch with low glucose equivalent, was prepared.

Specifically, 0.3 g of sodium hydroxide pellet was dissolved in 500 ml of purified water. Then, 1.0 g of ursodeoxycholic acid, 0.5 g of tauroursodeoxycholic acid, and 0.5 g of glycoursodeoxycholic acid were dissolved in the sodium hydroxide solution under stirring at room temperature. 60 g of maltodextrin was added little by little to the clear solution and stirred. A preservative was then added in an amount appropriate for the pharmaceutical formulation to the clear solution obtained by performing ultrasonication (750W, 20 kHz) at high throughput and the pH was adjusted by the dropwise addition of HCl.

Figure 5:
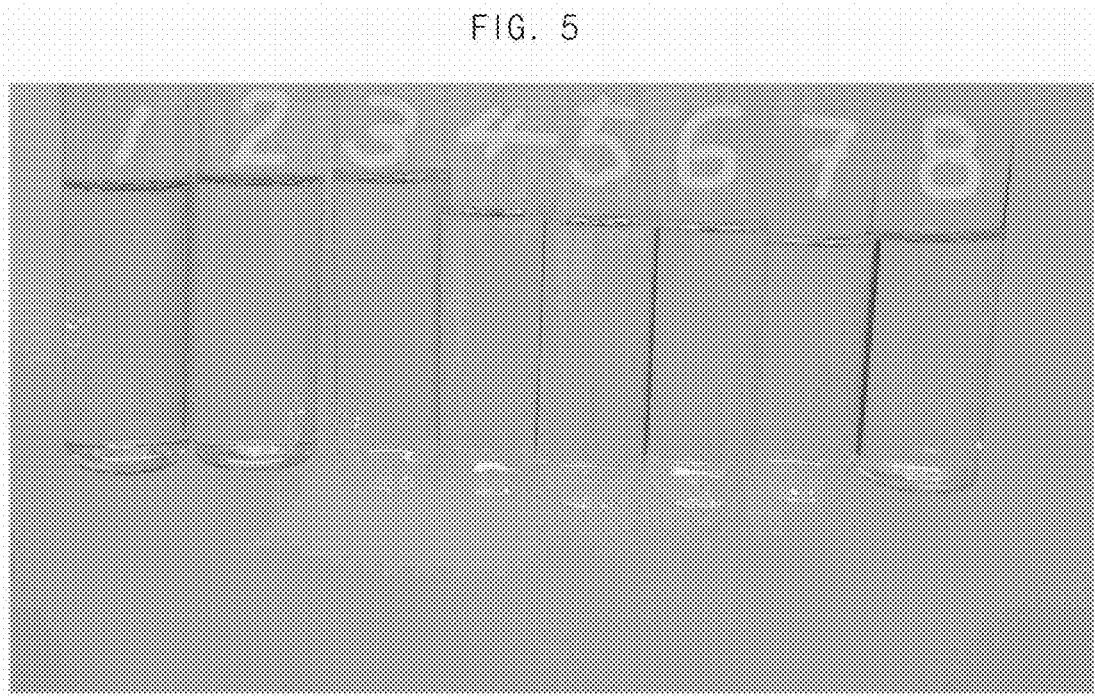
FIG. 5 illustrates whether a clear aqueous solution is formed or not based on pH value of the ursodeoxycholic acid solution prepared in Example 7 of this disclosure.

Purified water was added and adjusted to be a total of 1,000 ml. As shown in Table 1, the prepared ursodeoxycholic acid solution formed a clear aqueous solution at pH 10.2, 9.0, 8.1, 7.1, 6.1, 5.1, 4.1, and 2.9 without visual precipitation. FIG. 5 is images illustrating whether a clear aqueous solution of the ursodeoxycholic acid solution is formed or not at each pH value.

TABLE 1

Whether a clear aqueous solution was formed depending on the pH value of the ursodeoxycholic acid solution prepared according to each example

| Example | Weight ratio of UDCA to maltodextrin | Amount of ursodeoxycholic acid (g/L) | Amount of maltodextrin (g/L) | pH Value | Clarity | Remarks |
|---|---|---|---|---|---|---|
| 1 | 1:6 | 60 | 360 | 10.3 | Clear | |
|  |  |  |  | 9.2 | Clear | |
|  |  |  |  | 6.7 | Clear | |
|  |  |  |  | 5.4 | Precipitates | |
| 2 | 1:12 | 60 | 720 | 9.5 | Clear | |
|  |  |  |  | 7.3 | Clear | |
|  |  |  |  | 6.5 | Clear | |
|  |  |  |  | 6.1 | Clear | |
|  |  |  |  | 5.5 | Precipitates | |
| 3 | 1:15 | 50 | 750 | 9.5 | Clear | FIG. 1 |
|  |  |  |  | 8.9 | Clear | |
|  |  |  |  | 7.9 | Clear | |
|  |  |  |  | 7.1 | Clear | |
|  |  |  |  | 6.0 | Clear | |
|  |  |  |  | 5.5 | Precipitates | |
| 4 | 1:20 | 17.5 | 350 | 9.4 | Clear | FIG. 2 |
|  |  |  |  | 7.1 | Clear | |
|  |  |  |  | 6.1 | Clear | |
|  |  |  |  | 5.5 | Clear | |
|  |  |  |  | 5.1 | Precipitates | |
| 5 | 1:25 | 14 | 350 | 9.6 | Clear | FIG. 3 |
|  |  |  |  | 6.1 | Clear | |
|  |  |  |  | 5.1 | Clear | |
|  |  |  |  | 4.0 | Precipitates | |
| 6 | 1:30 | 25 | 750 | 9.0 | Clear | FIG. 4 |
|  |  |  |  | 8.0 | Clear | |
|  |  |  |  | 7.0 | Clear | |
|  |  |  |  | 6.0 | Clear | |
|  |  |  |  | 5.1 | Clear | |
|  |  |  |  | 4.1 | Clear | |
|  |  |  |  | 2.9 | Clear | |
| 7 | 1:30 | UDCA 1.0 g tUDCA 0.5 g gUDCA 0.5 g | 60 | 10.2 | Clear | FIG. 5 |
|  |  |  |  | 9.0 | Clear | |
|  |  |  |  | 8.1 | Clear | |
|  |  |  |  | 7.1 | Clear | |
|  |  |  |  | 6.1 | Clear | |
|  |  |  |  | 5.1 | Clear | |
|  |  |  |  | 4.1 | Clear | |
|  |  |  |  | 2.9 | Clear | |

Example 8. Preparation of a Skin Application Agent Containing Aqueous Solubilized ursodeoxycholic Acid The aqueous solubilized ursodeoxycholic acid in a clear aqueous solution prepared in Examples 1 to 7 was formulated into a skin application agent for the prevention or the treatment of inflammatory skin diseases or severe pruritus.

The skin application agent was prepared in the form of cream, lotion, serum, toner, essence and patch according to the formulation.

Formulation Examples

Formulation Example 1. Preparation of Skin Application Agent for Cream (1)

The aqueous solubilized ursodeoxycholic acid solution prepared in Example 6 (pH 7.0) was formulated into a skin application agent for testing skin absorption and atopic dermatitis improvement in the human body Table 2 (unit: wt %) shows the ingredients of the cream (1) composition. The composition may contain 0.1 to 5% of *Portulaca oleracea* extract and 0.1 to 5% of *Morus alba* bark extract.

The aqueous solubilized ursodeoxycholic acid solution in the prepared cream was well mixed with the ingredients of the skin application agent composition, not self-associated, and well characterized by emulsification without phase separation between the oil phase and the water phase even after a lapse of time.

TABLE 2

| Formulation Example 1 [Cream (1)] | |
|---|---|
| Ingredients | Cream (Formulation Example 1) |
| Composition of Example 6 | 15.0 |
| Carbomer | 13.0 |
| Butylene glycol | 4.0 |
| Caprylic/Capric triglyceride | 4.0 |
| Cetylethylhexane | 3.0 |
| Mineral oil | 3.0 |
| Cyclopentasiloxane | 3.0 |
| Polysorbate 60 | 1.2 |
| Cetearyl alcohol | 1.2 |
| Glycerol monostearate/PEG-100 stearate | 1.0 |
| Glyceryl monostearate | 1.0 |
| Macadamia seed oil | 1.0 |
| Dimethicone | 1.3 |
| Glyceryl monostearate | 0.5 |

TABLE 2-continued

Formulation Example 1 [Cream (1)]

| Ingredients | Cream (Formulation Example 1) |
|---|---|
| Stearic acid | 0.5 |
| Polyacrylamide/C13-14 isoparaffin/laureth-7 | 0.5 |
| Preservative, Coloring agent, Fragrance, Extracts | Appropriate amount |
| Purified water | Up to 100 |

Formulation Example 2. Preparation of Skin Application Agent for Cream (2)

The aqueous solubilized ursodeoxycholic acid solution prepared in Example 6 (pH 7.0) was formulated into a skin application agent for inhibiting sebum secretion and treating acne.

Table 3 (unit: wt %) shows the ingredients of the cream (2) composition. The composition may contain *Portulaca oleracea* extract 0.005 to 0.05 wt %, *Camellia sinensis* leaf extract 0.0001 to 0.001 wt %, *Centella asiatica* extract 0.5 to 2 wt %, *Cacao* extract 0.01 to 0.1 wt %, *Chamomilla recutita* flower extract 0.0001 to 0.001 wt %, and *Aloe vera* leaf extract 0.005 to 0.03 wt %.

The aqueous solubilized ursodeoxycholic acid solution in the prepared cream (2) was well mixed with the ingredients of the skin application agent composition, not self-associated, and well characterized by emulsification without phase separation between the oil phase and the water phase even after a lapse of time.

TABLE 3

Formulation Example 2 [Cream (2)]

| Ingredients | Cream (Formulation Example 2) |
|---|---|
| Composition of Example 6 | 5.0 |
| Dipropylene glycol | 8.0 |
| Cetylethyl hexanoate | 5.0 |
| PVP | 1.5~2.0 |
| Cetearyl alcohol | 1.5~2.0 |
| Cyclopentasiloxane | 1.8 |
| Glyceryl stearate SE | 1.0~1.5 |
| Glycerin | 1.0 |
| Shea butter | 1.0 |
| Betaglucan | 1.0 |
| Stearic acid | 1.0 |
| Carnauba wax | 0.5 |
| PEG-100 stearate | 0.5 |
| Glyceryl stearate | 0.5 |
| Phytosteryl/octyldodecyllaurylglutamate | 0.3 |
| Cetearyl glucoside | 0.24 |
| Preservative, Coloring agent, Fragrance, Extracts | Appropriate amount |
| Purified water | Up to 100 |

Formulation Example 3. Preparation of Skin Application Agent in the Form of Cream (3)

The aqueous solubilized ursodeoxycholic acid solution prepared in Example 6 (pH 7.0) was formulated into a test cream of skin application agent for the treatment of psoriasis.

Table 4 (unit: wt %) shows the ingredients of the cream (3) composition

The aqueous solubilized ursodeoxycholic acid solution in the prepared cream (3) was well mixed with the ingredients of the skin application agent composition, not self-associated, and well characterized by emulsification without phase separation between the oil phase and the water phase even after a lapse of time.

TABLE 4

Formulation Example 3 [Cream (3)]

| Ingredients | Cream (Formulation Example 3) |
|---|---|
| Composition of Example 6 | 10.00 |
| Glycerin | 10.00 |
| Caprylic/Capric triglyceride | 6.00 |
| isopropylisostearate | 4.00 |
| Stearyl alcohol | 2.50 |
| Dimethicone | 1.00 |
| Cetearyl alcohol | 1.00 |
| Polysorbate 80 | 0.75 |
| PEG-100 stearate | 0.75 |
| Glyceryl stearate | 0.75 |
| Sorbitan stearate | 0.60 |
| Ethylhexanediol | 0.48 |
| Tromethamine | 0.12 |
| Carbomer | 0.12 |
| Tocopheryl acetate | 0.12 |
| Glyceryl caprylate | 0.12 |
| Hydroxyethyl cellulose | 0.10 |
| Preservative, Coloring agent, Fragrance, Extracts | Appropriate amount |
| Purified water | Up to 100 |

Formulation Example 4. Preparation of Hydrogel Patch

The aqueous solubilized ursodeoxycholic acid solution prepared in Example 6 (pH 7.0) was formulated into a skin application agent in the form of hydrogel patch for testing skin permeability.

Table 5 (unit: wt %) shows ingredients of the hydrogel patch composition.

The aqueous solubilized ursodeoxycholic acid solution in the prepared hydrogel patch was well mixed with the components of the skin application agent composition, not self-associated in the hydrogel, and well characterized by emulsification without phase separation between the oil phase and the water phase even after a lapse of time.

TABLE 5

Components of Formulation Example 4(Hydrogel patch)

| Ingredients | Hydrogel patch (Formulation Example 4) |
|---|---|
| Composition of Example 6 | 20.0 |
| Glycerin | 19.0 |
| Polyvinylpyrrolidone | 10.0 |
| Propylene glycol | 8.0 |
| 1,2-hexanediol | 0.5 |
| Polysorbate 80 | 0.3 |
| Preservative, Coloring agent, Fragrance, Extracts | Appropriate amount |
| Purified water | Up to 100 |

Formulation Examples 5 to 9. Preparation of Skin Application Agent in Various Formulated Forms The aqueous solubilized ursodeoxycholic acid solution prepared in Example 6 (pH 7.0) was formulated into a Lotion (Formulation Example 5), a serum (Formulation Example 6), an essence (Formulation Example 7), a mask (Formulation Example 8), and a toner (Formulation Example 9).

Table 6 to Table 10 (unit: wt %) show ingredients of each composition, respectively.

The composition of Formulation Example 5 may contain 1 to 10 wt % of bacillus/bean/folic acid fermented extract, 0.5 to 5 wt % of *Morus alba* bark extract, 0.1 to 1 wt % of *Artemisia vulgaris* extract, and 0.5 to 1 wt % of *Citrus grandis* seed extract. The composition of Formulation Example 6 may contain 0.005 to 0.01 wt % of honey extract, 0.0005 to 0.01% of royal jelly extract, 0.005 to 0.1 wt % of *Hippophae rhamnoides* fruit extract, 0.01 to 0.1 wt % of *Cacao* extract, and 0.0001 to 0.001 wt % of *Chamomilla recutita* flower extract. The composition of Formulation Example 7 may contain 0.1 to 1 wt % of *Artemisia vulgaris* extract, 0.5 to 1 wt % of *Citrus grandis* seed extract, and 1 to 5 wt % of silver ear fungus extract. The composition of Formulation Example 8 may contain 0.05 to 1 wt % of *Guajava* leaf extract, 0.05 to 1% of *Camellia sinensis* leaf extract, 0.5 to 1 wt % of *Portulaca oleracea* extract, 0.05 to 1 wt % of witch hazel extract, and 0.05 to 0.5 wt % of *Rosa damascena* flower extract. The composition of Formulation Example 9 may contain 0.5 to 1 wt % of *Artemisia vulgaris* extract and 0.5 to 1 wt % of *Citrus grandis* seed extract.

Each aqueous solubilized ursodeoxycholic acid solution in the prepared formulated form was well mixed with the ingredients of the skin application agent composition, not self-associated, and well characterized by emulsification without phase separation between the oil phase and the water phase even after a lapse of time.

TABLE 6

Components of Formulation Example 5 (lotion)

| Ingredients | Lotion (Formulation Example 5) |
|---|---|
| Composition of Example 6 | 3.0 |
| Glycereth-26 | 12.0 |
| Butylene glycol | 7.0 |
| Cetylethyl hexanoate | 4.0 |
| Macadamia seed oil | 2.0 |
| Sorbitan stearate | 1.3 |
| Stearic acid | 1.3 |
| Glyceryl stearate | 1.0 |
| Dimethicone | 1.0 |
| Caprylic/Capric tryglyceride | 1.0 |
| Polysorbate 60 | 1.0 |
| Cetearyl alcohol | 0.6 |
| Octanediol | 0.4 |
| Glycerin | 0.3 |
| Arginine | 0.3 |
| Ethylhexyl glycerin | 0.2 |
| Carbomer | 0.2 |
| Pentaerythrityl tetra-di-t-butylhydroxyhydrocinnamate | 0.1 |
| Glyceryl polyacrylate | 0.1 |
| Preservative, Coloring agent, Fragrance, Extracts | Appropriate amount |
| Purified water | Up to 100 |

TABLE 7

Components of Formulation Example 6 (Serum)

| Ingredients | Serum (Formulation Example 6) |
|---|---|
| Composition of Example 6 | 3.0 |
| Butylene glycol | 8.5~9.5 |
| Cyclopentasiloxane | 3.5~4.5 |
| Dimethicone | 2.5~3.5 |
| PEG/PPG-17/6 copolymer | 2.5~3.5 |
| Glycerine | 2.0~3.0 |
| Polyglyceryl-3-methylglucose distearate | 1.5~2.5 |
| cyclohexasiloxane | 1.0~2.0 |
| Beta-glucan | 1.0~2.0 |
| Hydrocyanediol acrylate/sodium acryloyldimethyltaurate copolymer | 0.8 |
| Dimethicone | 0.6 |
| Palmitic acid | 0.5 |
| C12-16 alcohol | 0.2 |
| Preservative, Coloring agent, Fragrance, Extracts | Appropriate amount |
| Purified water | Up to 100 |

TABLE 8

Components of Formulation Example 7 (Essence)

| Ingredients | Essence (Formulation Example 7) |
|---|---|
| Composition of Example 6 | 3.0 |
| Glycereth-26 | 11.0 |
| Modified alcohol | 2.0 |
| PEG-40 hydrogenated castor oil | 0.6 |
| Glycerin | 0.5 |
| Octanediol | 0.3 |
| Carbomer | 0.2 |
| Polyacrylate-13 | 0.1 |
| Preservative, Coloring agent, Fragrance, Extracts | Appropriate amount |
| Purified water | Up to 100 |

TABLE 9

Components of Formulation Example 8 (Mask)

| Ingredients | Mask (Formulation Example 8) |
|---|---|
| Composition of Example 6 | 3.0 |
| Glycerin | 7.0 |
| Propanediol | 7.0 |
| 1,2-hexanediol | 2.0 |
| Trehalose | 1.0 |
| Polysorbate 80 | 0.6 |
| Xanthan gum | 0.4 |
| Sodium hyaluronate | 0.3 |
| Alatoin | 0.3 |
| Panthenol | 0.3 |
| PEG-40 hydrogenated castor oil | 0.5 |
| Arginine | 0.2 |
| Carbomer | 0.1 |
| Preservative, Coloring agent, Fragrance, Extracts | Appropriate amount |
| Purified water | Up to 100 |

TABLE 10

Components of Formulation Example 9 (Toner)

| Ingredients | Toner (Formulation Example 9) |
|---|---|
| Composition of Example 6 | 2.0 |
| Modified alcohol | 2.0 |
| Butylene glycol | 9.0 |
| Ethylhexyl glycerin | 0.1 |
| Octanediol | 0.1 |
| PEG-40 hydrogenated castor oil | 0.4 |
| Preservative, Coloring agent, Fragrance, Extracts | Appropriate amount |
| Purified water | Up to 100 |

Experimental Example 1. Test for In vitro Human Skin Permeability

In order to investigate the improvement of skin permeability of ursodeoxycholic acid when the form of crystalline ursodeoxycholic acid was formulated into the corresponding aqueous solubilized ursodeoxycholic acid formulations, the skin permeability of the ursodeoxycholic acid was measured using human cadaver skin in vitro using Franz diffusion cell according to OECD guidelines as follows.

Materials

Skin: stratum corneum of human cadaver skin (thickness of 80 mm)

Supplier: Hans Biomed Co., Ltd. (Korea)

Sample area: 0.636 $cm^2$

Receptor: PBS buffer (pH 7.4)

Analyte

Ursodeoxycholic acid (UDCA), which is eluted through the human cadaver skin

Analyzer and Conditions

Figure 6:
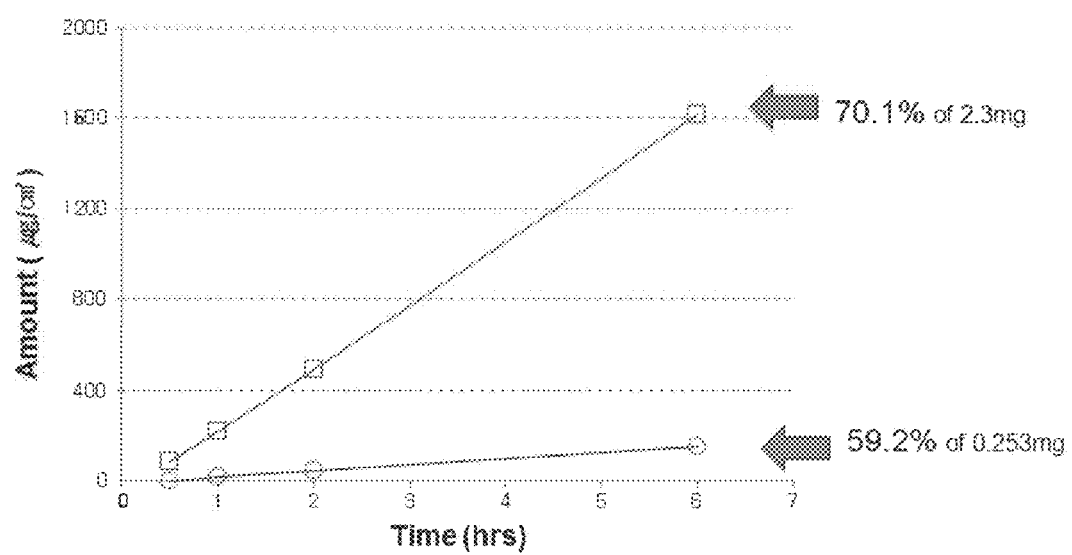
FIG. 6 is a graph illustrating the comparison of skin permeability of compositions in a cream formulation and in a patch formulation according to one embodiment of this disclosure wherein in FIG. 6, "☐" indicates composition in the form of cream (1) (Formulation Example 1)-Cream including 0.2925% of aqueous solubilized UDCA loading in 0.636 cm$^2$; and "○" indicates composition in the form of patch mask (Formulation Example 4)-Mask including 0.3898% of aqueous solubilized UDCA loading in 0.636 cm$^2$.

Agilent 1100 series HPLC according to an analysis method of ursodeoxycholic acid Results FIG. 6 is a graph illustrating each skin permeability when the aqueous solubilized ursodeoxycholic acid in a clear aqueous solution according to this disclosure is formulated into the skin application agent in the form of cream (1) (Formulation Example 1) and into the skin application agent in the form of hydrogel patch (Formulation Example 4). According to the experimental results, the skin permeability of the skin application agent in the form of cream (1) (Formulation Example 1) was 70.1% for a specific area of 0.636 $cm^2$ based on the concentration of the aqueous solubilized ursodeoxycholic acid. The skin permeability of the skin application agent in the form of hydrogel patch (Formulation Example 4) was 59.2%.

This result indicates that the aqueous solubilized ursodeoxycholic acid passes through the skin with a very high yield, compared to the characteristic of the conventional crystalline ursodeoxycholic acid which hardly passes through the skin.

Experimental Example 2. Human Skin Irritation Reaction Test

In order to investigate whether or not the skin irritation caused by crystalline ursodeoxycholic acid can be resolved when the form of ursodeoxycholic acid is changed to the corresponding aqueous solubilized ursodeoxycholic acid, human clinical trial for skin irritation reaction test was performed as follows.

The skin irritation reaction test was performed with the skin application agent prepared in various formulations on 31 subjects (Testing institution: Korea Institute for Skin and Clinical Sciences).

Test Material Application

Cream (2) (Formulation Example 2)

Lotion (Formulation Example 5)

Serum (Formulation Example 6)

Essence (Formulation Example 7)

Mask (Formulation Example 8)

Toner (Formulation Example 9)

Test Method

A skin patch test was performed on the subject using a Finn Chamber. The dorsal area of the subject was wiped with 70% ethanol and dried. 20 μl of a test material was dropped into the Finn Chamber having a diameter of 8 mm and were attached and fixed on an test area. In the case of the skin application agent of a liquid type essence (Formulation Example 6), a filter paper disc was placed in the Finn Chamber having a diameter of 8 mm, and then 20 μl of the test material was dropped and fixed on the test area. The patches were attached for 24 hours.

The degree of irritation was determined at 30 minutes, 24 hours, and 48 hours later after the patches were removed from the test area by a dermatologist according to the criteria of the International Contact Dermatitis Research Group (ICDRG).

Results

Test materials of Formulation Example 2 and Formulation Example 5 to Formulation Example 9 were applied on the human skin for 24 hours. The skin reaction at the test area was examined and classified depending on the degree of irritation at 30 minutes, 24 hours, and 48 hours later after the patches were removed from the skin according to the criteria of the International Contact Dermatitis Research Group. The mean score was read based on the results. In Formulation Example 2 and Formulation Example 5 to Formulation Example 9, no irritation was observed at 30 minutes, 24 hours, and 48 hours later after the removal of the patches, respectively. The mean score was 0.00 and evaluated as no irritation according to the criteria. Therefore, Formulation Example 2 and Formulation Example 5 to 9 were all found to belong to non-irritating skin application agents as a result of the human clinical trial for the safety evaluation by the skin patch test.

Conclusion

It was determined that the test materials of Formulation Example 2 and Formulation Example 5 to Formulation Example 9 according to this disclosure were all found to belong to non-irritating skin application agents as a result of the human clinical trial test for the safety evaluation by the skin patch test.

Therefore, according to this disclosure, it could overcome the disadvantage of the skin irritation when the crystalline ursodeoxycholic acid formulation was changed into to the aqueous solubilized ursodeoxycholic acid formulation.

Experimental Example 3. Acne Alleviating Test

The skin application agent in the form of essence (Formulation Example 7) was applied to 23 adults with acne for 8 weeks in order to examine whether acne was alleviated or not. The composition was applied twice a day on the facial area in equal amounts after cleansing (Clinical Trial Institution: Korea institute for Skin and Clinical sciences).

Evaluation Method

Experiment was conducted according to the standard operating procedure (SOP) of the Korea Institute for Skin and Clinical Sciences, and all procedures were checked by a person in charge of quality assurance service. The clinical study for evaluating suitability for acne-prone skin was conducted through (1) evaluation of suitability for acne-prone skin by visual assessment using Global Acne Grading System (GAGS), (2) evaluation of sebum excretion improvement using Sebumeter, (3) evaluation of abnormal skin response, and (4) survey.

Evaluation of Suitability for Use on Acne-Prone Skin (1) Evaluation of Suitability for Acne-Prone Skin by Visual Assessment Using the Global Acne Grading System (GAGS)

Visual evaluation of the suitability of a test material for the acne-prone skin was conducted by an investigator according to GAGS (FIG. 7A, FIG. 7B and FIG. 9A, and FIG. 9B). GAGS divides the face, chest and back into six areas (forehead, each cheek, nose, chin, chest and upper back), each of which is graded separately on a 0-4 scale (0=nil, 1=comedone, 2=papule, 3=pustule, 4=nodule) according to the severity of the acne lesion If multiple lesions were present in one area, the most severe lesions are evaluated. Based on the lesion score of each area derived here, the subject's acne class (1-18 points=mild, 19-30 points=moderate, 31-38 points=severe, 39 or above points=very severe) according to the total sum of the scores using GAGS This means that as the acne grade score decreases as compared to before use, it is suitable for acne-prone skin. The evaluation was made before and after two, four and eight weeks of the test material application.

(2) Evaluation of Sebum Improvement by Sebumeter

A sebumeter (SKIN-O-MAT, Cosmomed GmbH, Germany) was used to evaluate the sebum improvement on the acne-prone skin by test materials. A probing cassette with its sebum collecting tape was kept in contact with the left rounded side of the nose for 30 seconds at the same pressure to adsorb oil and then inserted to the instrument body to measure sebum amount. All procedures were performed by the same investigator. The Sebumeter analyzes the amount of oil excreted after attaching a special transparent sebum collecting tape to the skin using the principle of photometric reflection. The measurement unit is µg/cm$^2$ and the maximum value is 350. This means that as the measured value decreases as compared with that before the use of the test material, the sebum secretion is suppressed. Measurements were taken before and two, four and eight weeks of the test material application Statistical Analysis Statistical analysis of this experiment was performed using SPSS 17.0 for Windows program. The mean, standard deviation, frequency, and percentages were used to analyze the questionnaire of the subjects. A paired t-test analysis was performed to analyze the significant changes in the instrumentation results for various degrees of skin improvement.

Results

① Result of evaluation of suitability for acne-prone skin by visual assessment using the Global Acne Grading System (GAGS)

The principal investigator evaluated the suitability for acne-prone skin using the GAGS before and after two, four and eight weeks of use. As a result of visual evaluation of the suitability for acne skin the face using GAGS, the acne grade score was decreased by 7.19% after 2 weeks, 8.63% after 4 weeks, 8.99% after 8 weeks, compared to that before use. In addition, it was noted that the test materials had excellent effect on improving the acne-prone skin since the statistical significance was shown (p<0.05) after 2 weeks of use, after 4 weeks of use, and after 8 weeks of use compared to before use of the test materials (see FIG. 7A and FIG. 7B, and FIG. 9A and FIG. 9B).

Table 11 shows the changes in the acne grade score. Table 12 shows the improvement rate (%) of the acne grade score, and Table 13 shows the statistical analysis of the acne grade score, respectively.

TABLE 11

Changes in acne grade score

| | Global acne grading system score | | | |
|---|---|---|---|---|
| | before use | after 2 weeks of use | after 4 weeks of use | after 8 weeks of use |
| Mean | 12.09 | 11.22 | 11.04 | 11.0 |
| Standard deviation | 3.03 | 3.18 | 3.42 | 3.90 |

(0: none, 1~18: mild, 19~30: moderate, 31~38: severe, >39 very severe)

TABLE 12

Improvement rate (%) of acne grade score

| | after 2 weeks of use | after 4 weeks of use | after 8 weeks of use |
|---|---|---|---|
| Improvement rate (%) | 7.19 | 8.63 | 8.99 |

$$\text{Improvement rate (\%)} = \frac{\left[\begin{array}{l}\text{Measured value after use} - \\ \text{Measured value before use}\end{array}\right]}{\text{Measured value before use}} \times 100$$

TABLE 13

Statistical analysis of acne grade score

| | After 2 weeks of use | After 4 weeks of use | After 8 weeks of use |
|---|---|---|---|
| p-value | 0.040* | 0.023* | 0.020* |

*p < .05,
**p < .01,
***p < .001: p-value is measured by paired t-test

Figure 8A:
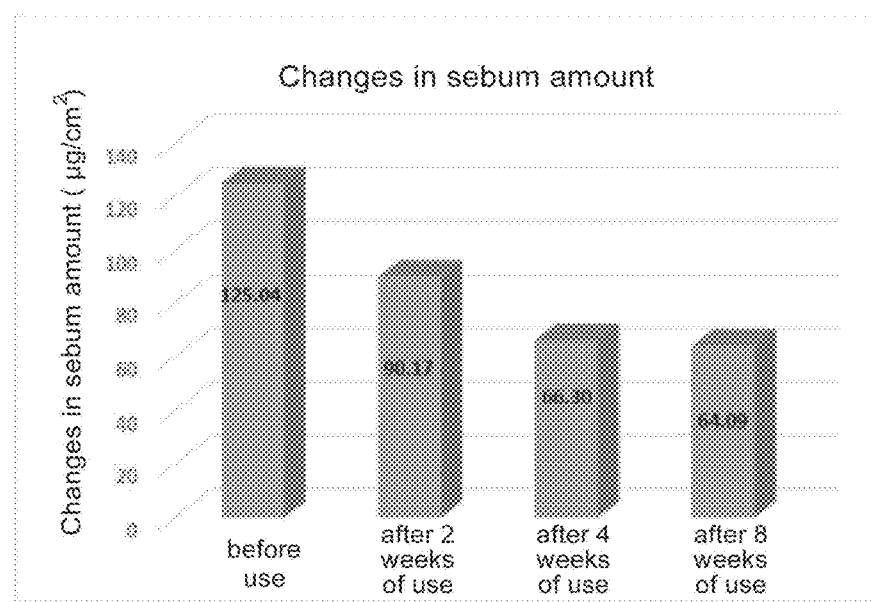
FIG. 8A and FIG. 8B are bar graphs illustrating the changes in sebum amount (A) and the improvement rates of sebum excretion (%, B) before using a composition, and 2 weeks, 4 weeks, and 8 weeks after using the composition according to one embodiment of this disclosure.
Figure 8B:
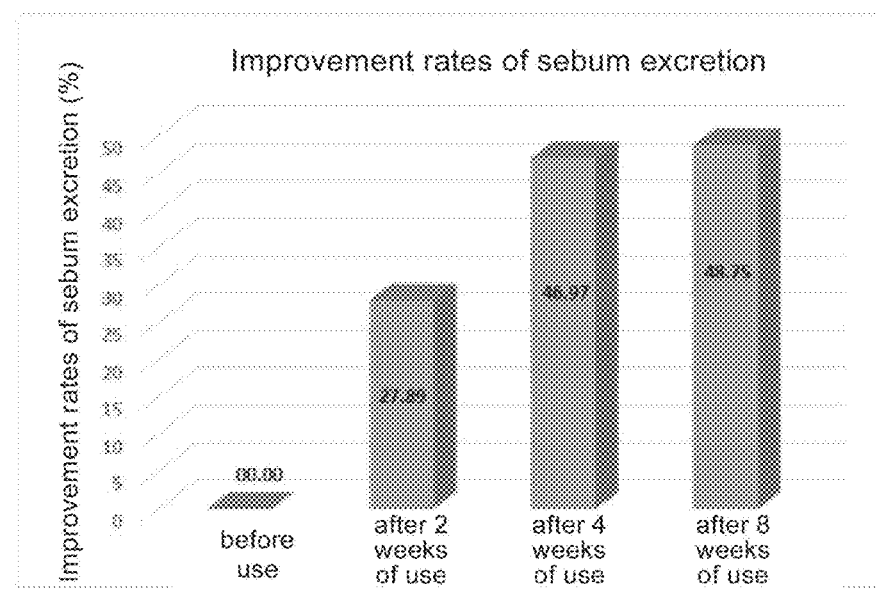
Figure 9A:
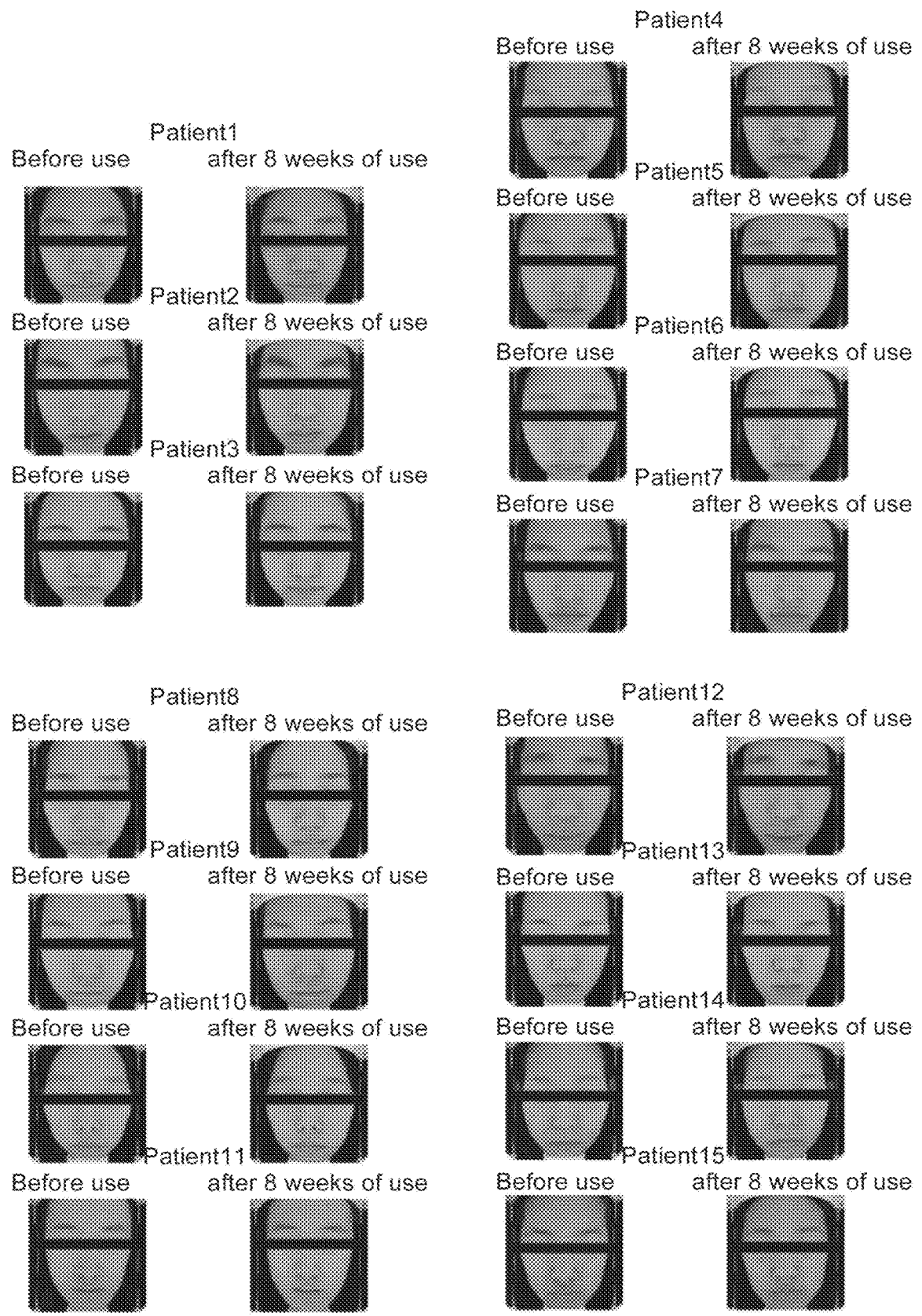
FIG. 9A and FIG. 9B are images illustrating the results obtained by applying a composition prepared in Example 2 to an acne-prone skin for 8 weeks and then taking a facial skin photographing system in order to determine the suitability for acne-prone skin.
Figure 9B:
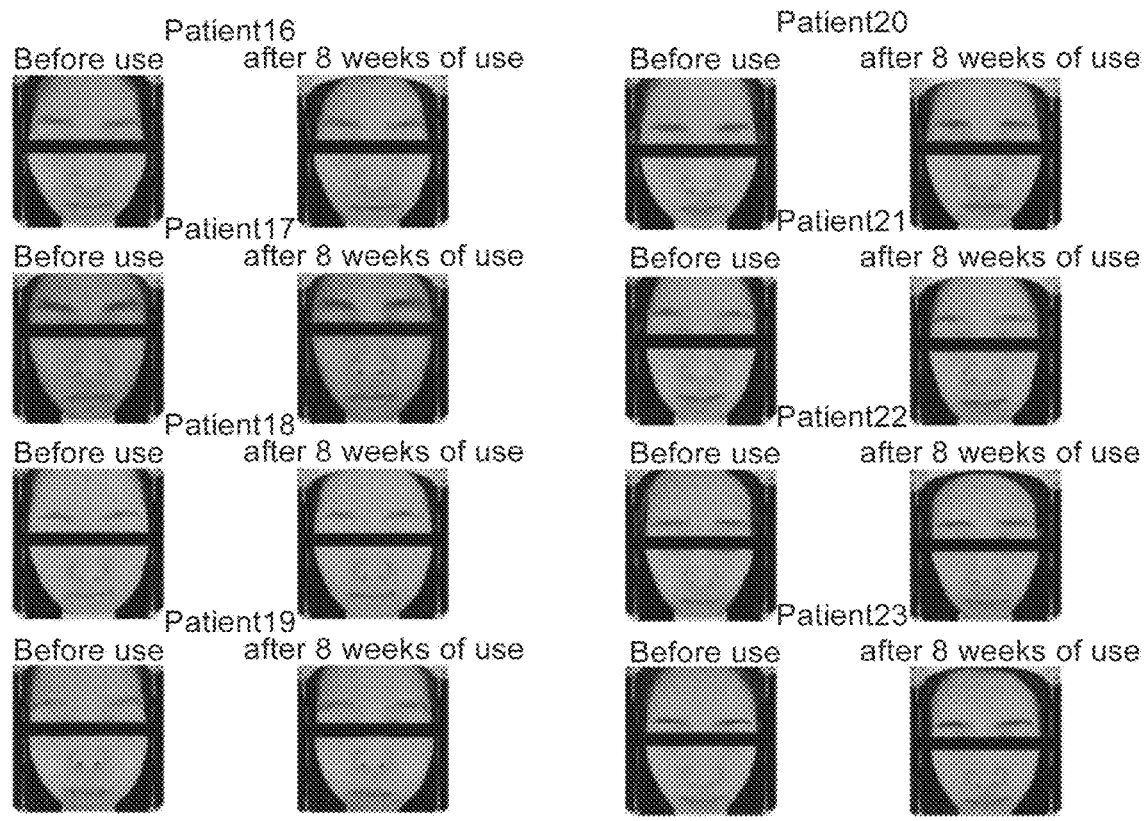

② Evaluation of sebum excretion improvement before and after the test material application The evaluation results of sebum excretion improvement on acne-prone skin before use and after two, four and eight weeks of test material application using Sebumeter are as follows (see FIG. 8A and FIG. 8B).

The evaluation results of sebum excretion improvement show 27.89%, 46.97% and 48.75% decrease after two, four and eight weeks of the teste material application respectively in comparison with the pre-application. In addition, it was noted that the test materials had excellent effect on the suppression of sebum excretion since statistical significance was shown after 2 weeks of use, after 4 weeks of use, and after 8 weeks of use (p<0.001) compared to before use of the test materials (see Table 14 to Table 16).

TABLE 14

Changes in sebum amount

| | Before use | After 2 weeks of use | After 4 weeks of use | After 8 weeks of use |
|---|---|---|---|---|
| Mean | 125.04 | 90.17 | 66.30 | 64.09 |
| Standard deviation | 53.06 | 48.93 | 39.53 | 40.66 |

Unit: µg/cm$^2$

TABLE 15

| | Improvement rate of sebum excretion (%) | | |
|---|---|---|---|
| | after 2 weeks of use | after 4 weeks of use | after 8 weeks of use |
| Improvement rate (%) | 27.89 | 46.97 | 48.75 |

$$\text{Improvement rate (\%)} = \frac{\left[\begin{array}{l}\text{Measured value after use} - \\ \text{Measured value before use}\end{array}\right]}{\text{Measured value before use}} \times 100$$

TABLE 16

| | Statistical analysis of sebum excretion | | |
|---|---|---|---|
| | After 2 weeks of use | After 4 weeks of use | After 8 weeks of use |
| p-value | 0.000*** | 0.000*** | 0.000*** |

*p < .05,
**p < .01,
***p < .001: p-value is measured by paired t-test (3) Evaluation of Abnormal Skin Response ① Evaluation of abnormal skin response There were no abnormal responses, including contact dermatitis or irritant contact dermatitis, after using the test materials on the subjects.

② Evaluation of abnormal skin response by survey of the subjects

In addition to the abnormal skin response evaluated by the investigator, the results of the questionnaire survey on the subject were as shown in Table 17, and no special abnormal skin response was observed in the questionnaire of the subjects.

TABLE 17

| | Abnormal skin response evaluated by subjects | | |
|---|---|---|---|
| Abnormal response | After 2 weeks of use | After 4 weeks of use | After 8 weeks of use |
| 1. Erythema (redness) | 0 | 0 | 0 |
| 2. Edema (swelling) | 0 | 0 | 0 |
| 3. Scales(keratin) | 0 | 0 | 0 |
| 4. Itching | 0 | 0 | 0 |
| 5. Pain | 0 | 0 | 0 |
| 6. Burning | 0 | 0 | 0 |
| 7. Stiffening | 0 | 0 | 0 |
| 8. Tingling | 0 | 0 | 0 |

0: None
1: Mild
2: Moderate
3: Severe (4) Survey of Subjects Before and After Using the Test Material ① Survey for general skin conditions of the subjects Survey with multiple-choice questionnaires was conducted for general skin characteristics of the subjects. The result is summarized in Table 18.

TABLE 18

| | General skin characteristics | | |
|---|---|---|---|
| | Questionnaires | Frequencies | Percentages (%) |
| Skin type | Oily | 7 | 30.4 |
| | Neutral (normal skin) | 4 | 17.4 |

TABLE 18-continued

| General skin characteristics | | |
|---|---|---|
| Questionnaires | Frequencies | Percentages (%) |
| Combination (T zone: oily; U zone: dry) | 11 | 47.8 |
| Dry | 1 | 4.4 |
| Sensitive | 0 | 0.0 |
| Total | 23 | 100.00 |

② Results of the subjects' skin condition characteristics before and after using the test material Survey with multiple choice or alternative questionnaires was conducted for skin condition characteristics of the subjects before using the test material. The result is summarized in Table 19.

TABLE 19

| Skin condition characteristics before using the test material | | | |
|---|---|---|---|
| Questionnaires | | Frequencies | Percentages (%) |
| Not have severe acne | Strongly disagree | 2 | 8.7 |
| | Disagree | 14 | 60.9 |
| | Neutral | 7 | 30.4 |
| | Agree | 0 | 0.0 |
| | Strongly agree | 0 | 0.0 |
| Not have redness and sensitiveness on acne spot | Strongly disagree | 3 | 13.0 |
| | Disagree | 18 | 78.3 |
| | Neutral | 2 | 8.7 |
| | Agree | 0 | 0.0 |
| | Strongly agree | 0 | 0.0 |
| Have moderate level of sebum excretion | Strongly disagree | 1 | 4.4 |
| | Disagree | 17 | 73.9 |
| | Neutral | 6 | 21.7 |
| | Agree | 0 | 0.0 |
| | Strongly agree | 0 | 0.0 |
| Have small and tightened pores | Strongly disagree | 3 | 13.1 |
| | Disagree | 15 | 65.2 |
| | Neutral | 5 | 21.7 |
| | Agree | 0 | 0.0 |
| | Strongly agree | 0 | 0.0 |
| Have smooth skin without roughness | Strongly disagree | 2 | 8.7 |
| | Disagree | 19 | 82.6 |
| | Neutral | 2 | 8.7 |
| | Agree | 0 | 0.0 |
| | Strongly agree | 0 | 0.0 |
| Total | | 23 | 100.0 |

③ Survey of subjects' usage feeling after the test material application

Survey with alternative questionnaires of satisfied/dissatisfied was conducted for subjects' feeling after use of test material. The result is summarized in Table 20.

TABLE 20

Usage feeling after the test material application

| Questionnaires | Answers | After 2 weeks of use | | After 4 weeks of use | | After 8 weeks of use | |
|---|---|---|---|---|---|---|---|
| | | Frequencies | Percentages (%) | Frequencies | Percentages (%) | Frequencies | Percentages (%) |
| Texture | Satisfied | 22 | 96.7 | 23 | 100.0 | 23 | 100.0 |
| | Dissatisfied | 1 | 4.3 | 0 | 0.0 | 0 | 0.0 |
| Feeling of application | Satisfied | 23 | 100.0 | 23 | 100.0 | 23 | 100.0 |
| | Dissatisfied | 0 | 0.0 | 0 | 0.0 | 0 | 0.0 |
| absorption | Satisfied | 23 | 100.0 | 20 | 87.0 | 21 | 91.3 |
| | Dissatisfied | 0 | 0.0 | 3 | 13.0 | 2 | 8.7 |
| Moistness | Satisfied | 17 | 73.9 | 19 | 82.6 | 18 | 78.3 |
| | Dissatisfied | 6 | 26.1 | 4 | 17.4 | 5 | 21.7 |
| Soothing | Satisfied | 19 | 82.6 | 21 | 91.3 | 22 | 95.7 |
| | Dissatisfied | 4 | 17.4 | 2 | 8.7 | 1 | 4.6 |
| Overall satisfaction | Satisfied | 22 | 96.7 | 23 | 100.0 | 23 | 100.0 |
| | Dissatisfied | 1 | 4.3 | 0 | 0.0 | 0 | 0.0 |

④ Results of the subjects' skin condition characteristics after using the test material Survey with multiple choice questionnaires was conducted for skin condition characteristics of the subjects after using the test material. The result is summarized in Table 21.

TABLE 21

Skin condition characteristics after the test material application

| Questionnaires | | After 2 weeks of use | | After 4 weeks of use | | After 8 weeks of use | |
|---|---|---|---|---|---|---|---|
| | | Frequencies | Percentages (%) | Frequencies | Percentages (%) | Frequencies | Percentages (%) |
| Acne was relieved | Strongly disagree | 0 | 0.0 | 0 | 0.0 | 0 | 0.0 |
| | Disagree | 2 | 8.7 | 2 | 8.7 | 0 | 0.0 |
| | Neutral | 13 | 56.5 | 9 | 39.1 | 8 | 34.8 |
| | Agree | 8 | 34.8 | 11 | 47.8 | 12 | 52.2 |
| | Strongly agree | 0 | 0.0 | 1 | 4.4 | 3 | 13.0 |
| Redness and sensitiveness on acne spot was relieved | Strongly disagree | 0 | 0.0 | 0 | 0.0 | 0 | 0.0 |
| | Disagree | 2 | 8.7 | 2 | 8.7 | 0 | 0.0 |
| | Neutral | 9 | 39.1 | 3 | 17.4 | 5 | 21.7 |
| | Agree | 10 | 43.5 | 15 | 65.2 | 16 | 69.6 |
| | Strongly agree | 2 | 8.7 | 2 | 8.7 | 2 | 8.7 |
| Sebum excretion was decreased | Strongly disagree | 0 | 0.0 | 0 | 0.0 | 0 | 0.0 |
| | Disagree | 1 | 4.3 | 2 | 8.7 | 1 | 4.3 |
| | Neutral | 10 | 43.5 | 8 | 34.8 | 4 | 17.4 |
| | Agree | 12 | 52.2 | 9 | 39.1 | 12 | 52.2 |
| | Strongly agree | 0 | 0 | 4 | 17.4 | 6 | 26.1 |
| Pore size was decreased | Strongly disagree | 0 | 0.0 | 0 | 0.0 | 0 | 0.0 |
| | Disagree | 3 | 13.0 | 3 | 13.0 | 1 | 4.3 |
| | Neutral | 12 | 52.2 | 12 | 52.2 | 14 | 60.9 |
| | Agree | 7 | 30.4 | 5 | 21.8 | 6 | 26.1 |
| | Strongly agree | 1 | 4.4 | 3 | 13.0 | 2 | 8.7 |
| Skin became smooth with decreased skin roughness | Strongly disagree | 0 | 0.0 | 0 | 0.0 | 0 | 0.0 |
| | Disagree | 3 | 13.0 | 2 | 8.7 | 1 | 4.4 |
| | Neutral | 8 | 34.8 | 4 | 17.4 | 5 | 21.7 |
| | Agree | 9 | 39.2 | 14 | 60.9 | 13 | 56.5 |
| | Strongly agree | 3 | 13.0 | 3 | 13.0 | 4 | 17.4 |
| Total | | 23 | 100.0 | 23 | 100.0 | 23 | 100.0 |

As described above, the skin external preparation containing the clear aqueous solution of aqueous solubilized ursodeoxycholic acid was evaluated for suitability for use against acne-prone skin. As a result, there was statistically significant (p<0.05) improvement of acne grade score such as increases of 7.19% after 2 weeks, 8.63% after 4 weeks, 8.99% after 8 weeks, and statistically significant (P<0.001) improvement rate of sebum excretion such as increases of 27.89% after 2 weeks, 46.97% after 4 weeks, 48.75% after 8 weeks, compared to before the use of the test material.

In addition, no adverse reactions to allergic contact dermatitis or irritant contact dermatitis were observed from the subjects during the test period, and no specific skin abnormal responses were observed according in the questionnaire to the subjects.

Therefore, the skin application agent containing the aqueous solubilized ursodeoxycholic acid solution showed, without causing skin irritation, the effects of acne treatment and improvement rate in sebum secretion.

Experimental Example 4. Relieving Effect of Atopic Dermatitis

In order to confirm the effect of atopic dermatitis relief, 22 patients with atopic dermatitis was applied cream (1) type skin application agent (Formulation Example 1) on each arm area. The skin application agent was applied to the affected part twice a day, and the mitigation effect of atopic dermatitis was evaluated after 1 week.

Experiment Summary

Object: Verification of effectiveness in atopic dermatitis of the skin external preparation containing the aqueous solubilized ursodeoxycholic acid (Formulation Example 1).

Method: Application on affected area

Duration: 7 days

Subjects: 22 patients with atopic dermatitis

Table 22 shows the severity of atopic symptoms in patients with atopic dermatitis who participated in the experiment (95% of 22 patients with severe and moderate atopic dermatitis)

TABLE 22

Atopic symptoms in patients with atopic dermatitis

| | Symptom | | | |
|---|---|---|---|---|
| | Severe | Moderate | Almost none | Total |
| No. of patient | 11 | 10 | 1 | 22 |
| Percentages | 50% | 45% | 5% | 100% |

Results

1) For all patients with atopic dermatitis: the higher the score for each category, the better the evaluation (the highest score: 5 points, see Table 23).

TABLE 23

Evaluation of the skin external preparation for all patients

| Categories | Results |
|---|---|
| Moisturizing during use | 4.1 |
| Absorption | 4.0 |
| Stickiness | 2.5 |
| Moisture persistency | 3.9 |
| Alleviation of itching | 3.6 |
| Alleviation of atopy | 3.4 |
| Skin irritation | 4.4 |
| Satisfaction after use | 3.8 |
| Average | 3.7 |

2) For 11 subjects with severe atopic symptoms: the higher the score, the better the evaluation (the highest score: 5 points, see Table 24).

TABLE 24

Evaluation of the skin external preparation for patients with severe symptoms

| Categories | Results |
|---|---|
| Moisturizing during use | 4.2 |
| Absorption | 4.2 |
| Stickiness | 2.4 |
| Moisture persistency | 3.9 |
| Alleviation of itching | 3.9 |
| Improvement of atopic symptoms | 3.5 |
| Skin irritation | 4.4 |
| Satisfaction after use | 4.0 |
| Average | 3.8 |

Analysis

Figure 10:
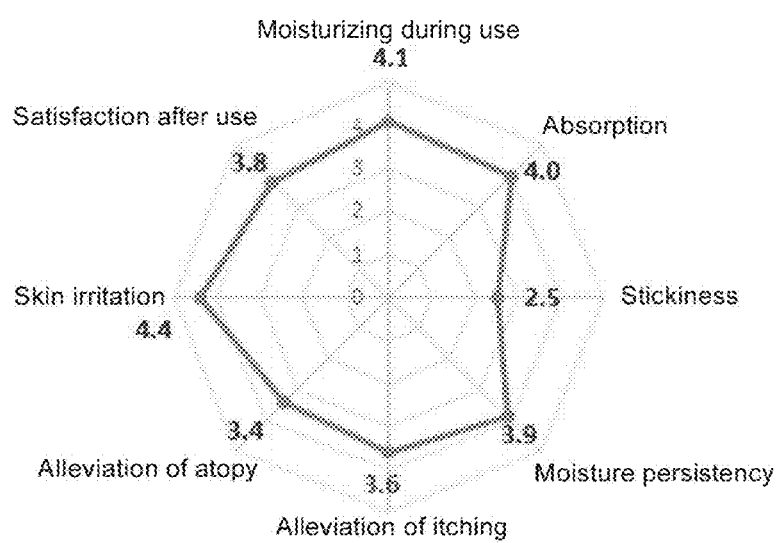
FIG. 10 is a diagram illustrating the quality evaluation results of the skin external preparation for all patients with atopic dermatitis using the composition in the form of cream (1) (Formulation Example 1) according to this disclosure.
Figure 11:
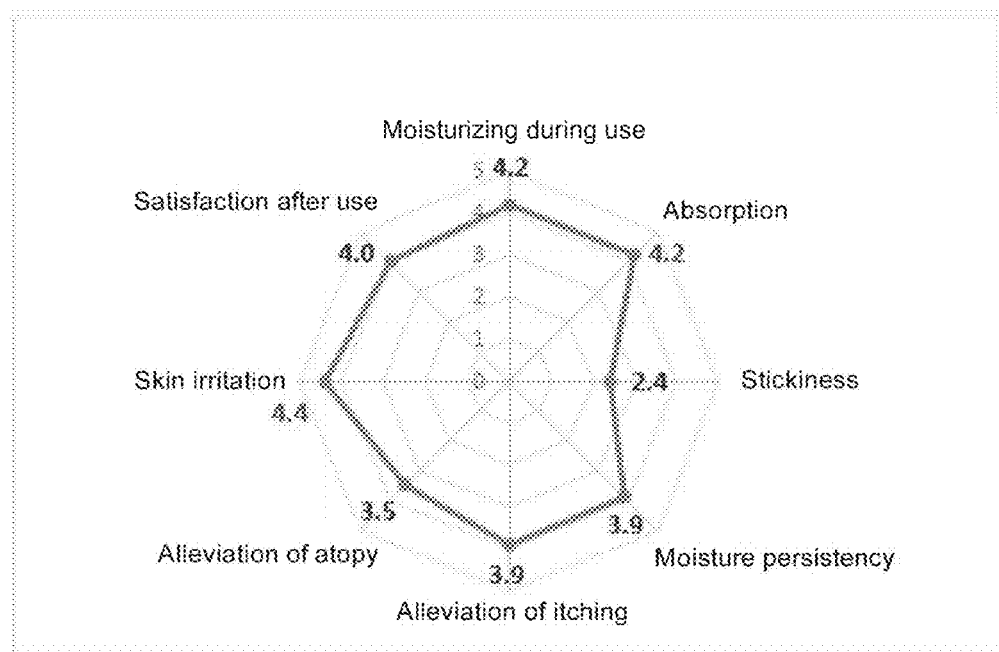
FIG. 11 is a diagram illustrating the quality evaluation results of the skin external preparation for eleven patients with severe atopic symptoms among all patients with atopic dermatitis using the composition in the form of cream (1) (Formulation Example 1) according to this disclosure.

As a result of the evaluation for all atopic dermatitis patients, the highest score (4.4 points) was graded in skin irritation, which is the most important quality factor of atopic care products, resulted in no skin irritation. The Improvement of atopic symptoms was scored for 3.5, alleviation of itching was scored for 3.9, and overall satisfaction was relatively high of 4.0 (FIG. 10). In addition, 11 patients with severe atopic symptoms showed a 0.3 point higher rate of itching than all patients with atopic dermatitis (FIG. 11).

Conclusion

It is confirmed that the skin application agent containing the aqueous solubilized ursodeoxycholic acid in a clear aqueous solution exhibits its effect on atopic dermatitis by showing alleviation of itching and alleviation of atopic symptoms, which are the most important factors in atopy care, from the evaluation with 22 patients. It is also confirmed that the skin application agent containing the aqueous solubilized ursodeoxycholic acid exhibits its effect on atopic dermatitis by showing alleviation of atopic dermatitis as well as high alleviation of itching, which is the most important factor in atopic care, from the evaluation with 11 patients with severe atopic dermatitis (see FIG. 10 and FIG. 11).

Experimental Example 5: Effect of Alleviating and Treating psoriasis Symptoms

Effect of the skin application agent containing the aqueous solubilized ursodeoxycholic acid was examined for treating psoriasis using an animal model in order to develop a new drug for psoriasis treatment. The skin application agent in the form of cream was applied three times a day on the back of a mouse which is psoriasis-induced with 5% imiquimod cream and the mitigation effect of psoriasis symptoms was confirmed from day 1 to 11 days (Testing institute: Institute for drug evaluation affiliated with Qu-BESTBIO Co., Ltd.).

Experiment Summary

Object: To determine the effect of the skin application agent containing the aqueous solubilized ursodeoxycholic acid on psoriasis.

Test Cream: In order to develop a new drug for the treatment of psoriasis, the aqueous solubilized ursodeoxycholic acid in a clear aqueous solution prepared in Example 6 was formulated into a test cream (3) of a skin external preparation. Ingredients of the test cream (3) composition is shown in Table 4 (unit: wt %).

Method: It was applied to psoriatic lesions. 62.5 mg of 5% imiquimod was applied once a day to the dorsal area which is depilated. The skin external preparation was applied to the skin 2 hours before the inducing agent was applied.

Duration: 11 days progressed

Subjects: G1 group (5 female mice) was applied with Vaseline cream for 11 days, G2 group (8 female mice) was applied with 5% imiquimod cream for 8 days, G3 group (8 female mice) was applied with 5% imiquimod cream for 8 days and also applied with the test cream from day 5 to day 11 (FIG. 12).

Results

Figure 13A:
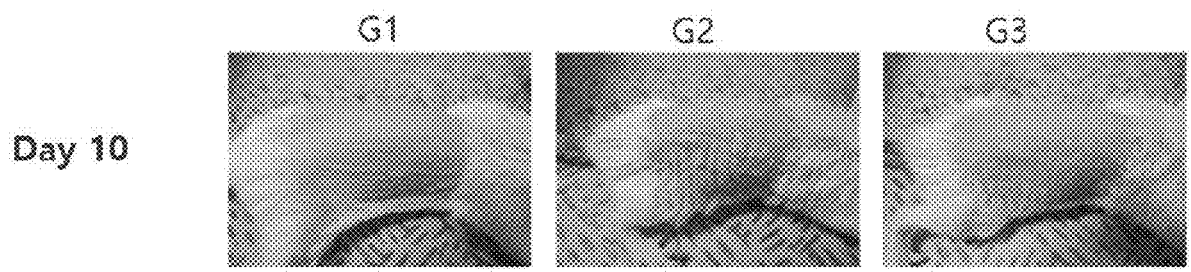
FIGS. 13A, 13B and 13C illustrate the results of an efficacy test in a psoriasis animal model according to this disclosure.

1) Clinical symptoms of psoriasis-induced area were visually evaluated by an investigator on a 0-4 scale depending on the disease activity index (DAI) of Table 24 (Table 25 and FIG. 13A).

TABLE 25

Disease activity index
Disease activity index (DAI)
Erythema, Scales, Thickening (Score: 0~4)

| 0 | None |
|---|---|
| 1 | Slight |
| 2 | Moderate |
| 3 | Marked |
| 4 | Very marked |

Figure 13B:
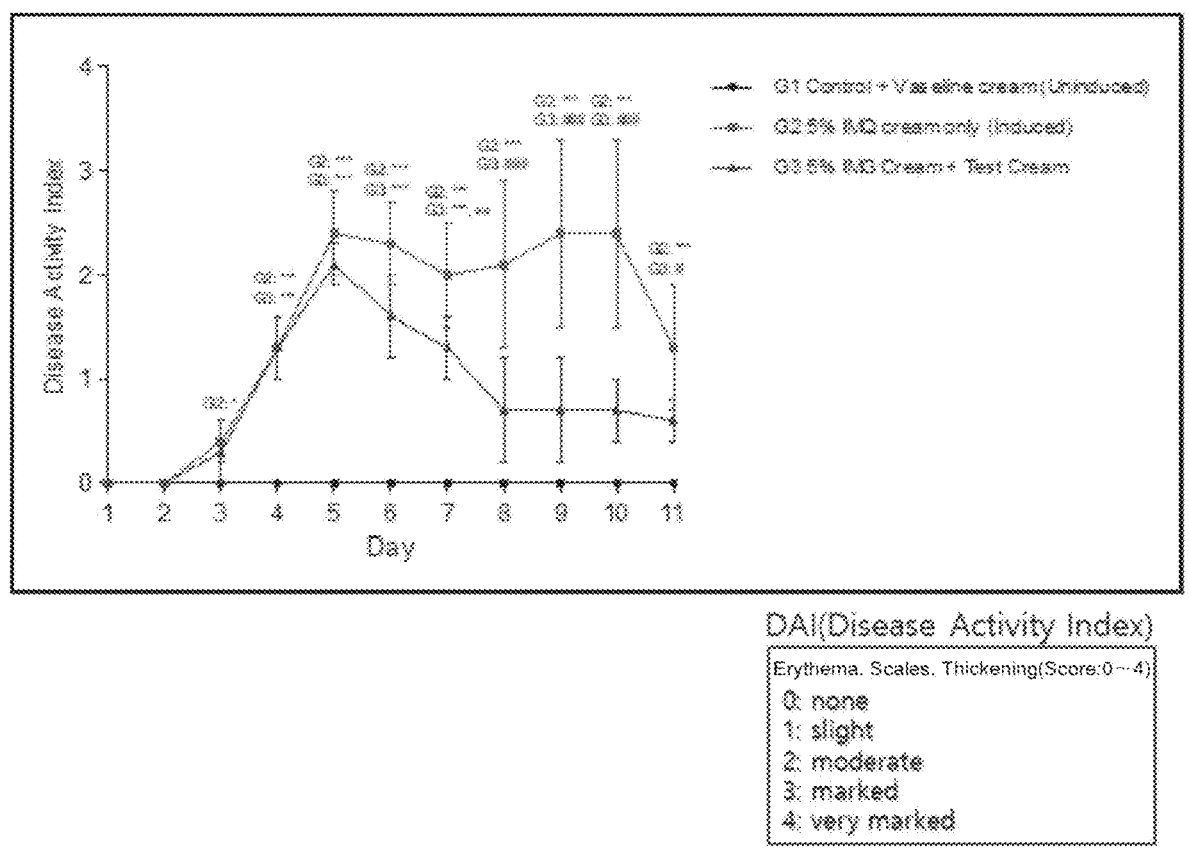

2) The disease activity index was 0 in the G1 group applied with Vaseline cream for 11 days and 2.4 in the G2 group applied with 5% imiquimod cream for 8 days, while it was 0.7 in the G3 group applied with 5% imiquimod cream for 8 days and also applied with the test cream from day 5 to day 11. Symptoms of psoriasis in the G3 group was significantly alleviated since the disease activity index of the G3 group was almost close to the disease activity index of the control G1 group applied with Vaseline cream only (FIG. 13B). The disease activity index of the G3 group was statistically significant (p<0.05-p<0.001).

Figure 13C:

3) The degree of epidermal hyperkeratosis in the skin of the experimented mice was observed to be about 140% higher in the group (G2) in which the 5% imiquimod cream was applied for 8 days compared with the group (G1) in which the Vaseline cream was applied. On the other hand, in the group (G3) coated with the test cream, the level was almost the same as that of the control group at 114%, which significantly lowered the symptoms of epidermal hyperkeratosis induced by imiquimod (see Table 26 and FIG. 13C).

TABLE 26

Thickness of stratum corneum (μM)

| Group | G1 (Vaseline Cream) | G2 (5% IMQ cream) | G3 (5% IMQ Cream + Test cream) |
|---|---|---|---|
| Animals No. | 5 | 5 | 5 |
| 1 | 16.12 ± 8.67 | 17.68 ± 5.24 | 11.16 ± 1.94 |
| 2 | 13.68 ± 7.66 | 16.27 ± 9.37 | 12.50 ± 3.72 |
| 3 | 11.08 ± 3.27 | 15.81 ± 6.60 | 14.72 ± 2.63 |
| 4 | 13.86 ± 5.22 | 17.96 ± 4.37 | 19.15 ± 9.37 |
| 5 | 8.43 ± 5.28 | 20.64 ± 6.75 | 14.29 ± 4.10 |
| Mean ± SD | 12.63 ± 2.95 | 17.67 ± 1.89 | 14.36 ± 3.03 |

Results

Test cream, a skin application agent for the development of new drug for the treatment of psoriasis containing the aqueous solubilized ursodeoxycholic acid, showed anti-psoriasis efficacy when applied to the psoriasis skin of mouse three times a day for 7 days.

Experimental Example 6: Effect of Alleviating and Treating dermatitis Symptoms

The inhibitory effect of inflammatory reactions, which is the main symptom of various inflammatory skin diseases, was confirmed (Testing institute: Laboratory Animal Resource Center of Korea Research Institute of Bioscience and Biotechnology).

First, phorbol 12-myristate 13-acetate (TPA), which is an inflammation inducing substance, was prepared at a concentration of 15 μg/ml and applied to the back of the mouse ear by 20 μl. Test material was the aqueous solubilized ursodeoxycholic acid (YSB301), a new drug candidate for inflammatory skin diseases. The concentration of ursodeoxycholic acid was prepared to be 0.625%, 1.25% and 2.5% and applied 30 minutes before TPA treatment on the same area by 20 μl.

Experiment Summary

Object: To determine the effects of a new drug candidate (YSB301) comprising the aqueous solubilized ursodeoxycholic acid on inflammatory skin diseases.

Test material: The aqueous solubilized ursodeoxycholic acid in a clear aqueous solution (pH 7.0) of Example 6 was designated as "a new drug candidate for inflammatory skin diseases (YSB301)" and diluted with purified water to be the concentration of ursodeoxycholic acid 0.625%, 1.25%, 2.5% (wt. %) as shown in Table 27. In the case of vehicle, only ursodeoxycholic acid was excluded in Example 6.

TABLE 27

Changes in ear thickness

| Test material | UDCA conc. (wt %) | Maltodextrin conc. (wt %) |
|---|---|---|
| YSB301 2.5% | 2.5 | 75.0 |
| YSB301 1.25% | 1.2 | 75.0 |
| YSB301 0.625% | 0.625 | 75.0 |
| Vehicle | 0 | 75.0 |

Method: 20 μl of TPA (15 μg/ml), which is an inflammation inducing substance, was applied to the back of a mouse ear, and the degree of increase in ear thickness was measured from 0 hr to 4 hr. The new drug candidate for inflammatory skin diseases (YSB301) and the vehicle were applied to the back of mouse ear, then after 30 minutes, 20 μl of the inflammation inducing substance TPA was applied to the same spot.

Duration: proceed for 4 hours

Subjects: Six female mice that were not treated with anything, six female mice that induced inflammation by TPA after application of vehicle only, and 18 female mice (three groups) that induced inflammation by TPA after application of new drug candidate (YSB301).

Results

Figure 14:
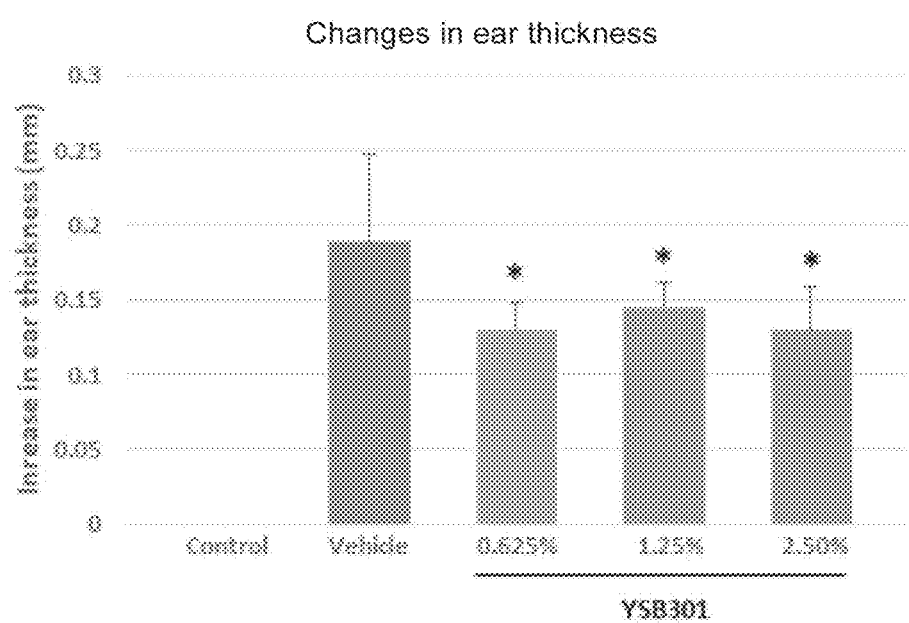
FIG. 14 is a bar graph illustrating the results of an efficacy test of an aqueous solubilized ursodeoxycholic acid against inhibition of the inflammatory reaction, which is the main symptom of various inflammatory skin diseases, in an acute dermatitis animal model according to this disclosure, wherein the changes in thickness of ear inflamed by phorbol 12-myristate 13-acetate are determined.

As shown in FIG. 14, a vehicle and the new drug candidate for inflammatory skin diseases (YSB301) were applied and the ear thickness of mouse with inflammation induced by TPA was measured. As a result, there was statistically significant (p<0.05) inhibition effect on inflammation, which was 31% for ursodeoxycholic acid concentration of 0.625%, 23.4% for ursodeoxycholic acid concentration 1.25%, and 31.2% for ursodeoxycholic acid concentration 2.5% as compared with that of the mouse treated with the vehicle.

Conclusion

The skin application agent including the aqueous solubilized ursodeoxycholic acid can effectively be used to treat a variety of inflammatory skin diseases such as atopy, psoriasis and eczema by effectively alleviating inflammation which is a major symptom of various inflammatory skin diseases.

The spirit of the present disclosure has been described by way of example hereinabove, and the present disclosure may be variously modified, altered, and substituted by those skilled in the art to which the present disclosure pertains without departing from essential features of the present disclosure. Accordingly, the exemplary embodiments disclosed in the present disclosure and the accompanying drawings do not limit but describe the spirit of the present disclosure, and the scope of the present disclosure is not limited by the exemplary embodiments and accompanying drawings. The scope of the present disclosure should be interpreted by the following claims and it should be interpreted that all spirits equivalent to the following claims fall within the scope of the present disclosure.

What is claimed is:

1. A skin treatment cream for treatment of psoriasis comprising:
  a composition comprising:
  at least one bile acid salt selected from an ursodeoxycholic acid (UDCA), a tauroursodeoxycholic acid and a glycoursodeoxycholic acid;

an aqueous soluble starch conversion product; and
water, wherein the composition has pH values of 2.9-9.0, the skin treatment cream further comprising:
Carbomer mixed with the composition;
Caprylic/Capric triglyceride mixed with the composition and having a weight percentage less than that of the composition;
isopropylisostearate, Stearyl alcohol, Dimethicone, and Cetearyl alcohol, all mixed with the composition, the isopropylisostearate having a weight percentage greater than that of the Stearyl alcohol, the Stearyl alcohol having a weight percentage greater than that of the Cetearyl alcohol; and
one or more of PEG-100 stearate, Glyceryl stearate, Sorbitan stearate, Ethylhexanediol, Tromethamine, or Tocopheryl acetate, mixed with the composition,
wherein the Carbomer has a weight percentage less than that of the composition,
wherein the Carbomer has a weight percentage less than that of the Caprylic/Capric triglyceride, and
wherein the aqueous soluble starch conversion product is maltodextrin and the weight ratio of the at least one bile acid salt to the maltodextrin is 1:30.

2. The skin treatment cream of claim 1, wherein the one or more of PEG-100 stearate, Glyceryl stearate, Sorbitan stearate, Ethylhexanediol, Tromethamine, or Tocopheryl acetate, comprise all of PEG-100 stearate, Glyceryl stearate, Sorbitan stearate, Ethylhexanediol, Tromethamine, and Tocopheryl acetate, all mixed with the composition.

3. The skin treatment cream of claim 1, wherein the one or more of PEG-100 stearate, Glyceryl stearate, Sorbitan stearate, Ethylhexanediol, Tromethamine, or Tocopheryl acetate, comprise all of PEG-100 stearate, Glyceryl stearate, Sorbitan stearate, and Ethylhexanediol, all mixed with the composition.

4. The skin treatment cream of claim 3, wherein the PEG-100 stearate has a weight percentage same as that of the Glyceryl stearate, the Glyceryl stearate having a weight percentage greater than that of the Sorbitan stearate, the Sorbitan stearate having a weight percentage greater than that of the Ethylhexanediol.

5. The skin treatment cream of claim 2, wherein the Tromethamine and the Tocopheryl acetate have same weight percentage.

* * * * *